United States Patent [19]

Lautenschläger

[11] Patent Number: 5,447,077

[45] Date of Patent: Sep. 5, 1995

[54] DEVICE FOR THE EVAPORATION TREATMENT OF PREFERABLY LIQUID SUBSTANCES, IN PARTICULAR REAGENTS, OR FOR THE PREPARATION OR ANALYSIS OF SAMPLE MATERIAL

[75] Inventor: Werner Lautenschläger, Leutkirch, Germany

[73] Assignee: MLS Mikrowellen-Labor-Systeme GmbH, Leutkirch, Germany

[21] Appl. No.: 170,295

[22] PCT Filed: Apr. 29, 1993

[86] PCT No.: PCT/EP93/01037

§ 371 Date: Dec. 30, 1993

§ 102(e) Date: Dec. 30, 1993

[87] PCT Pub. No.: WO93/22650

PCT Pub. Date: Nov. 11, 1993

[30] Foreign Application Priority Data

Jul. 14, 1992 [DE] Germany ............... 42 23 116.7
Apr. 30, 1992 [DE] Germany ............... 42 14 392.6

[51] Int. Cl.⁶ ............................................. G01N 25/00
[52] U.S. Cl. ................................. 73/863.11; 422/102
[58] Field of Search ........... 73/863.23, 863.11, 863.12; 422/68.1, 78, 58, 102

[56] References Cited

U.S. PATENT DOCUMENTS

| | | | |
|---|---|---|---|
| 4,347,216 | 8/1982 | Kawasaki et al. | 422/78 |
| 4,693,867 | 9/1987 | Commarmot et al. | 422/64 |
| 5,135,872 | 8/1992 | Pouletty et al. | 422/58 |
| 5,192,984 | 3/1993 | Beecher et al. | 356/433 |
| 5,201,232 | 4/1993 | Uffenheimer | 73/864.23 |
| 5,270,010 | 12/1993 | Lautenschaläger | 422/102 |

FOREIGN PATENT DOCUMENTS

| | | |
|---|---|---|
| 0156742 | 10/1985 | European Pat. Off. . |
| 0335020 | 10/1989 | European Pat. Off. . |
| 0467625 | 1/1992 | European Pat. Off. . |
| 3818697 | 12/1992 | Germany . |
| 2081442 | 2/1982 | United Kingdom . |

*Primary Examiner*—Richard E. Chilcot, Jr.
*Assistant Examiner*—Max H. Noori
*Attorney, Agent, or Firm*—Fitzpatrick, Cella, Harper & Scinto

[57] ABSTRACT

In a device (1) for the evaporation treatment of preferably liquid substances, in particular reagents, or for the preparation or analysis of sample material in a container (6), having a preferably microwave-operated heating appliance (2) and a holder (4) for at least one container (6) in the heating chamber (3), the container (6) being connected to a supply line (11; 11a) and/or to a discharge line (9; 63, 63a), the line (9; 11; 11a; 63; 63a) has in the peripheral region of the container (6) a releasable line connection (43; 45) which is established by the insertion movement on insertion of the container (6) into the holder (4) or severed by the removal movement on removal of the container (6) from the holder (4) as a result of coaxial relative displacement or parallel displacement of the line connection portions (38a, 38b; 23c).

17 Claims, 11 Drawing Sheets

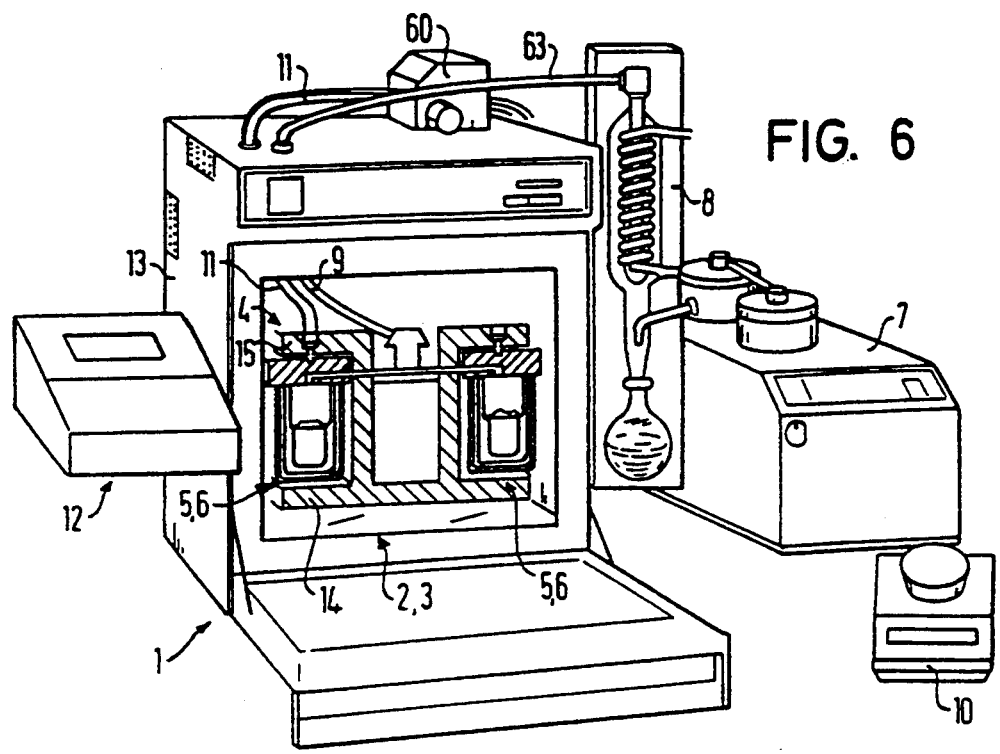
FIG. 6
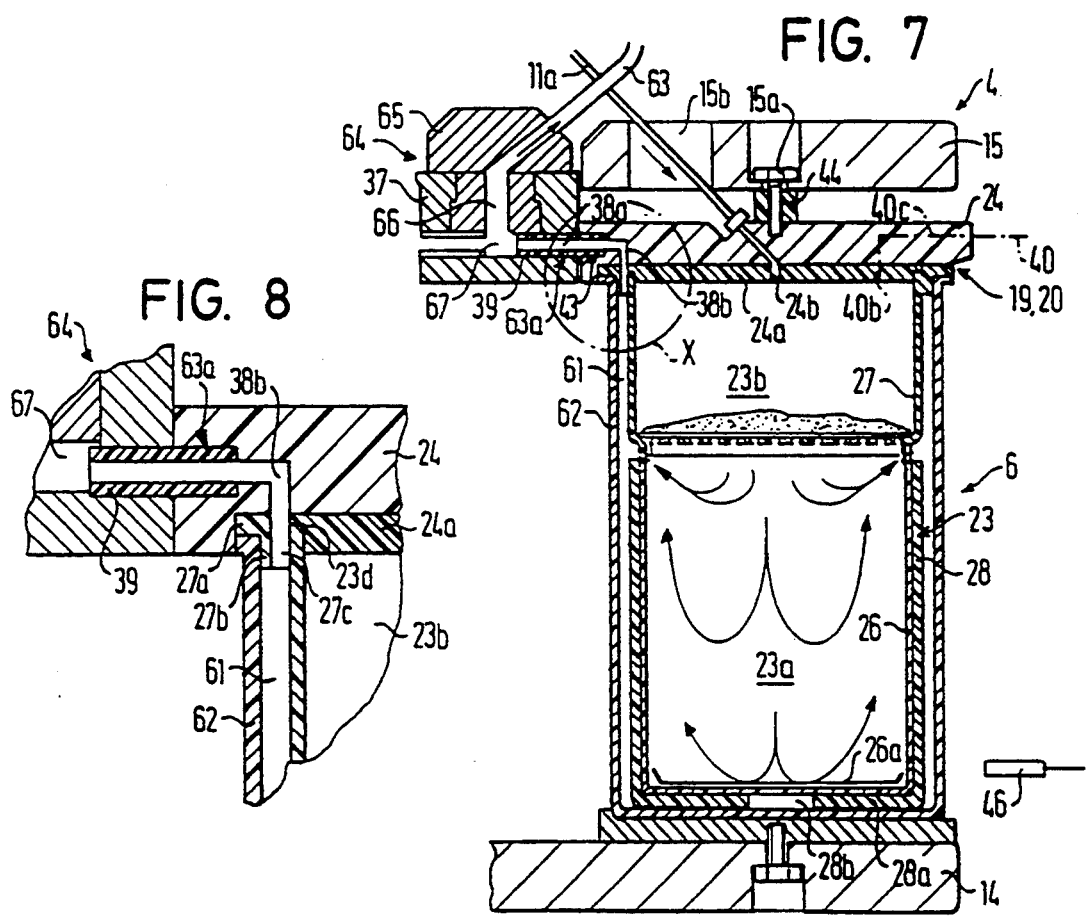
FIG. 7
FIG. 8

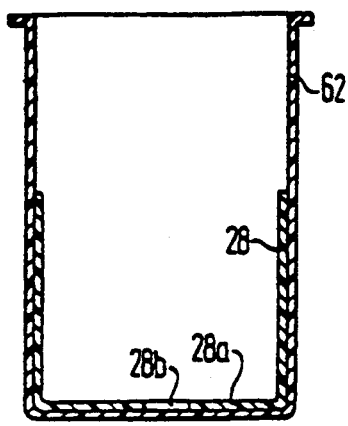
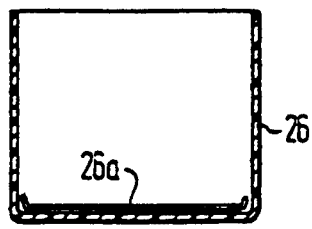
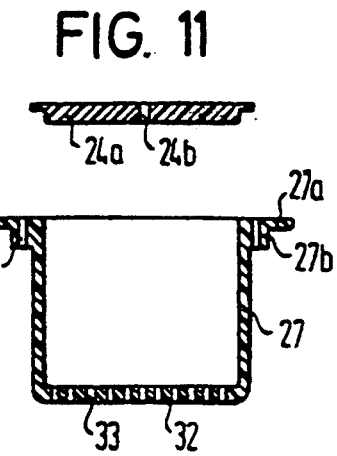
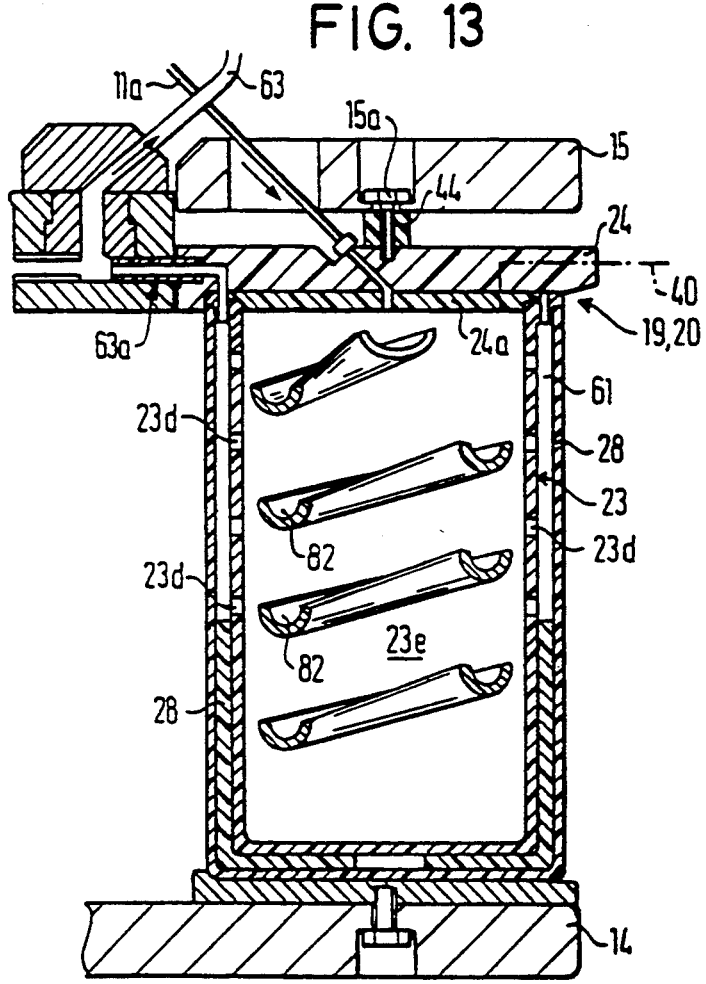

DEVICE FOR THE EVAPORATION TREATMENT OF PREFERABLY LIQUID SUBSTANCES, IN PARTICULAR REAGENTS, OR FOR THE PREPARATION OR ANALYSIS OF SAMPLE MATERIAL

BACKGROUND OF THE INVENTION

1. Field of the Invention

It is common practice, particularly in analytical chemistry, to utilize evaporation of a substance, particularly a reagent such as, fox: example, a liquid solvent, to separate preselected constituents of the substance.

For said purpose, the substance is heated in a container in order to bring about accelerated evaporation. Certain conclusions may then be drawn from the residual constituents, e.g. by considering the weight or weights thereof.

Owing to the separation effect which occurs during the evaporation of evaporable fractions of a substance, it is advantageously possible through the evaporation also to separate a substance into specific constituents or also to purify a substance of specific constituents. The invention therefore also relates to the field of application of distillation.

Evaporation and/or preparation may occur under a partial vacuum or excess pressure in the container.

To accelerate the evaporation and/or preparation, the substance to be evaporated is heated, this usually entailing a pressure increase in the container.

2. Description of the Related Art

DE-OS 38 18 697 describes a heating appliance for heating and preparing sample material in at least one container under excess pressure, where, upon a pressure increase in the container as described above, the resulting gases may upon a specific pressure being exceeded escape through a pressure relief valve of the container, pass into the closed heating chamber and be extracted from there by means of an extraction device. It has also already been proposed to remove the resulting vapours or gases by means of a pipe connected directly to the container and possibly subject them to analytical evaluation.

In the case of the evaporation measures described above, the substance may be situated in a specific quantity in the container or it may by means of a substance supply line and a vapour removal line be continuously supplied and/or removed as vapour. In many cases of analytical chemistry, however, it is usual to introduce the substance into the container in a specific quantity, e.g. after weighing, and to remove the vapour or gas arising during the treatment by means of a vapour removal line.

All of the cases described above involve frequent handling of the container, e.g. for introducing the substance or removing treatment residues. However, any attempt to make handling simpler and quick is frustrated by the line connection of the container, particularly in cases where the at least one container during heating in the associated appliance is rotated or swivelled back and forth, as is the case with the above-mentioned heating appliance disclosed in DE-OS 38 18 697. In known constructions, before the container is removed or inserted in the heating appliance, the existing line connection has to be separately opened or closed, which makes handling more difficult. Furthermore, particularly in the case of a rotating holder for the at least one container, the arrangement of the line is problematical.

SUMMARY OF THE INVENTION

The object of the invention is to design a device of the type described initially in such a way as to enable user-friendly and fast insertion and removal of the container into and out of the heating appliance.

This is achieved, in one aspect, by providing a line, which may be either or both a supply line and a discharge line, which is connected or released by the insertion movement or removable movement of the container from a holder as a result of relative displacement of portions of the line connection.

In the device according to the invention, the line connection to and/or from the container may be automatically established by inserting the container into its positioning point in the holder and automatically severed by removing the container. There is therefore no need to operate a special screw connection or execute a special movement for closing or opening the line connection, which would be user-unfriendly and time-consuming and would moreover require an increased level of attention on the part of the operator.

Preferably, in the construction according to the invention, a guide for the direction of movement of the container, especially during insertion, is associated with the holder so that the operator does not have to worry too much about whether the container is in the correct position when being inserted or pushed into the holder. The guide positively conveys the container into its predetermined position, with the end position of the container also being definable in a simple manner by means of a movement stop.

In the context of the invention, it is possible for the axis of the line connection to extend transversely or at right angles to the (approximately) horizontal insertion and removal movement or to extend in a longitudinal direction or parallel to the horizontal insertion and removal movement. In the former case, a parallel displacement of the axial portions of the line connection is effected until they are aligned with one another. In the latter case, the line connection according to the invention may be formed by a plug-in connection in the peripheral region of the container with one plug-in connection part in the holder and one plug-in connection part associated with the container, said plug-in connection parts cooperating with one another in the manner of a coupling. In both cases, the insertion and removal movement of the container is used to establish and sever the line connection automatically.

In both cases indicated above, a sealing of the line connection may be realized in a simple manner. In the first case, horizontal contiguous fitting surfaces may be disposed between the holder and the container or a ring seal may be disposed between a downward-directed surface of the holder and an upward-directed surface of the container, said ring seal surrounding the point of separation of the line connection in the form of a ring.

In the context of the invention, it is further possible for the line connection according to the invention to be formed by a line portion extending in the holder and a line portion extending in the lid of the container or merely by a line portion extending in the holder. In the latter case, when a pot-shaped container is used, the lid of the container may be formed by the holder, in which case the preferably vertical connection line portion extending in the holder-side lid part thus formed emanates from or opens out into the cavity of a pot-shaped container.

The invention also relates to advantageous container constructions in various versions. One construction, as already described above, is such that an open-topped pot-shaped container is provided and a lid part associated with said container is associated with the holder or is a part of the holder.

Another container construction is such that the container is formed by a top container part and a bottom container part, with a sieve or filter plate being provided between the container parts for receiving the sample material, the cavity of the bottom container part preferably being able to be acted upon by a partial vacuum.

The measure of effecting evaporation in the presence of a partial vacuum is advantageous in all embodiments basically because a partial vacuum lowers the boiling point of the reagent or solvent and so it is possible to operate not only with less heating energy but also at lower temperatures, thereby allowing gentle treatment of the sample material or enabling the treatment of heat-sensitive material. As a result, evaporation may occur more effectively both in general and in particular when, in the case of a two-piece container as described above, the partial vacuum is applied to the cavity of the bottom container part while a sample impregnated with the reagent or solvent is situated above and an air stream generated by the extraction system is conveyed through the sample.

In the context of the invention, it is possible for the heating chamber accommodating at least one container to be acted upon as a whole by a partial vacuum and evacuated or for the container, or each container, to be directly evacuated or for each container to be disposed in a separate partial-vacuum container or chamber in the heating chamber, so that in each case only the partial-vacuum container surrounding the container with a slight clearance need be evacuated, this taking less energy and time to achieve.

The invention also relates to an advantageous gas sweeping device for the container or containers for removing vapours or the like, with it being possible for the reagent or solvent to be introduced into the container prior to insertion of the container into the holder or to be supplied preferably automatically by a supply device when the container has already been inserted into the holder. In the latter case, it is advantageous to combine an introduction of gas or air enabling extraction of the vapours with the supply for the reagent. Means may be provided, which allow gas or air to be introduced even when no reagent is to be supplied, because in many cases only a batch-wise supply of reagent is desired. Both are effected preferably through the lid of the container or through a part of the holder forming a lid for the container.

It is advantageous, in the case of extraction of the vaporous constituents in the container, to associate with the container or the heating chamber an aeration valve through which a gas or air may be sucked in. A sweeping action and improved removal of the vaporous constituents are thereby achieved. When an inert gas is used as an aerating or sweeping gas, explosion protection for flammable materials in the container may also be achieved.

The invention is suitable both for automatic and manual introduction of the reagent or solvent in the container, with particularly in the case of an automatic supply this being able to be effected continuously or alternatively in one batch, preferably during charging of the container.

In all cases there is a need to recognize when the evaporation process has ended. In said regard also, solutions are proposed in the form of a method and associated devices. Firstly, it is proposed that the pressure in the container or in its lines should be monitored and that, in the event of a pressure drop greater than a specific amount or a pressure drop which, within a specific period of time, exceeds a specific rate of pressure drop, the heating should be reduced or switched off. Alternatively or additionally, it is possible for said purpose also to measure the temperature of the vapour in or at the container and, in the event of a temperature rise above a specific level or in the event of a temperature rise above a predetermined rate, to reduce or switch off the heating. The invention further relates to devices for effecting said methods.

A further aspect of the invention relates to the manufacture of the container, parts of the container or supplementary parts which surround the container, from a material which is heated by the microwave radiation and as a result heats the material in the container. Such a construction is advantageous not only because microwave-permeable material may be treated but also because, after the microwave radiation has been reduced or switched off, it is ensured that the material will continue to be heated or kept hot, so that there can be no rise in vapour pressure or a temperature drop—which could invalidate determination of the end point—as would otherwise occur as a result of cooling.

The solutions according to the invention are eminently suitable for a holder, for the at least one container, which rotates or may swivel back and forth, e.g. through 360°. A rotating holder requires a revolving joint for the line to enable a continuous supply and/or removal through the line despite rotation of the holder. The holder is preferably equipped to receive a plurality of containers, with the line branching off preferably in the region of the revolving joint to the positioning points for the containers and with the same number of line connections being provided as there are positioning points.

When evaporating preferably liquid substances or preparing or analysing sample material, the at least one container is exposed to a considerable temperature which sets in as a result of heating of the sample material and/or container material by the microwaves and/or possibly also a chemical reaction in the container. Temperatures of around 200° C. to 500° C. or higher may arise. At high temperatures, stability problems occur with regard to the container and/or holder material, particularly when said material is a resistant plastic material such as, preferably, polytetrafluoroethylene (PTFE Teflon). The stability problem is exacerbated by the fact that, in a known device of the type indicated in the already cited DE-OS 38 18 697, the lid of the container is prestressed towards the bottom container part. At a high operating temperature, namely when the stability of the container material decreases, said prestressing leads to an additional stressing of the container, resulting in deformation or damage and malfunctions. Further problems addressed by the invention are therefore the high operating temperature and the resultant stability problems for the at least one container and/or the holder. The latter problem arises, especially when the holder guarantees closure of the container, mainly when operating with excess pressure.

Further aspects of the invention for solving the above-mentioned problems are, on the one hand, to reduce the temperature acting upon the container and/or holder and/or to reduce the stress on the container and/or holder. A feature which solves the first-mentioned problem consists of sweeping the heating chamber with air and hence cooling the container and/or holder externally and/or internally. A further solution feature is to support at least one container on the holder in a suspended arrangement. By said means, there is not only a substantial reduction in the stresses acting upon the container but also an enlargement of the external cooling surface of the container because the underside of the container may also be cooled. In said regard it should be noted that, especially with the cooperation of a reagent, the operating temperature is highest in the bottom region of the container.

The invention also relates to a cooling device, by means of which the holder and/or the container or containers or parts thereof may be cooled. The risk of thermal overload exists particularly for the container and indeed mainly for the bottom container part which contains the sample material heated by the microwaves. The other parts of the device situated in the heating chamber may be simultaneously cooled, or alternatively only the holder could be cooled, namely by the cooling air flow which traverses the heating chamber from the cooling air inlet of said chamber.

The construction according to the invention is particularly suitable for evaporation and preparation treatments under excess pressure. With such treatment measures in particular, extremely high temperatures develop in the container.

The invention is however also suitable for treatments of material in the sample container which are effected with a partial vacuum and during which the reaction chamber in the container is evacuated and at the same time the reaction chamber is aerated with a view to achieving as complete a pneumatic sweeping of the reaction chamber as possible. During said process, an internal cooling of the container is effected, and said cooling may be combined with an external cooling when the suction air flow is directed from the interior of the container towards its exterior.

The invention also relates to measures enabling an improved analysis result. The analysis result may in many cases be corrupted by the formation of condensation product in the container, particularly after completion of the evaporation or preparation process. An aspect of the invention is therefore to prevent or reduce the formation of condensation product in the container or to provide measures preventing condensation product from reaching the sample residue provided for analysis. The formation of condensation product may be reduced by generating heat in the top region of the container, i.e. at its lid or in the region of its top edge, this being achievable by the arrangement, possibly on additional parts, of materials which are microwave-absorbent and so are heated during operation by the microwave.

Another measure according to the invention consists of providing in the container at least one receiving area for condensation product, into which condensation product automatically flows. Particularly when a bottom container part is laterally removed without the lid from the holder, any condensation product clinging to the lid will be scraped off and fall onto the residual sample material. In a further refinement of the invention, a peripheral groove for receiving the condensation product is provided in the container, and is provided in particular on an adapter ring.

The sub-claims contain features which contribute to problem-solving, lead to constructions which are simple, practical and hence inexpensive to manufacture, improve handling, assembly, dismantling, sealing, thermal economy and operation and also prolong the service life.

BRIEF DESCRIPTION OF THE DRAWINGS

The invention and further advantages achievable by the invention are described in greater detail hereinafter with reference to preferred embodiments and drawings. The drawings show:

FIG. 6 a perspective front view of a device according to the invention in a modified construction;

FIG. 7 a vertical section through a container of the device according to FIG. 6 in its inserted position in the device;

FIG. 8 an enlarged view of the detail labelled X in FIG. 7;

FIGS. 9–12 details of the multi-part container according to FIG. 7, likewise in vertical section;

FIG. 13 and 14 modified constructions of the device in sectional views corresponding to FIG. 2;

DETAILED DESCRIPTION OF THE PREFERRED EMBODIMENTS

Figure 1:
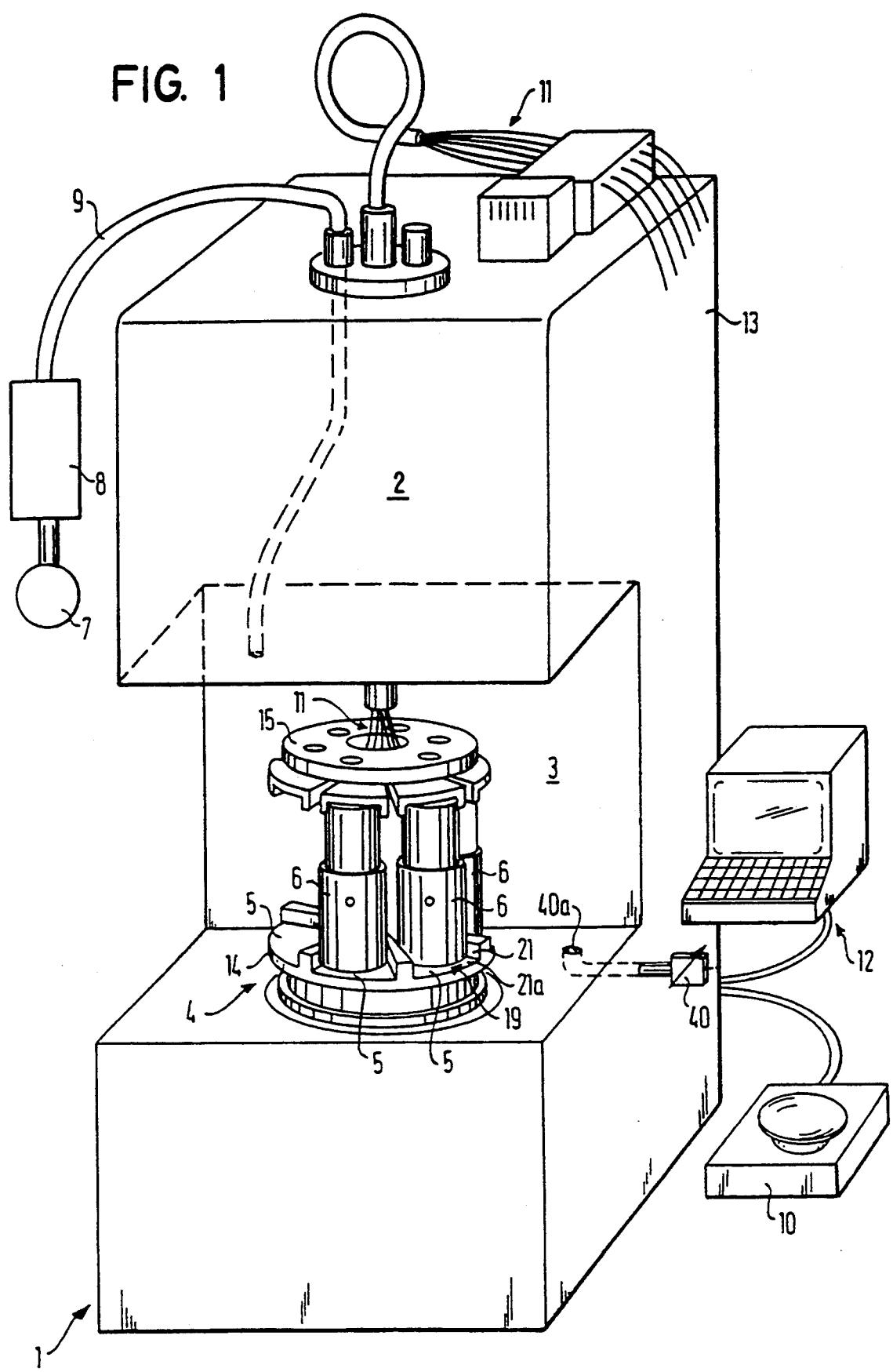
FIG. 1 a simplified perspective front view of a device according to the invention for evaporating in particular liquid substances, preferably reagents, or for preparing or analysing sample material in at least one container which is to be selectively opened and closed.

The principal parts of the device 1 are a heating appliance 2 preferably operating with microwaves and having a heating chamber 3 closable, for example, by means of a door (not shown), a holder 4 disposed therein and having a plurality of—preferably four or six—positioning points 5 for containers 6, a suction pump 7, a condensation cooler 8 disposed in the suction line 9 leading to the suction pump 7, a plurality of supply lines 11—or a common supply line branching into a plurality of supply lines—for a solvent, and an electronic control device 12 preferably having a computer and being capable of working according to preset or entered programs, a keyboard and a display or a display screen for displaying control data preferably being associated with the control device 12. Further associated with the device 1 is a balance 10 which is situated outside of the heating chamber 3, the balance preferably being an electronic balance 10 which is connected by an electric control line to the control device 12. The latter may be integrated into the device or be disposed in the housing containing the keyboard and the display screen.

Figure 2:
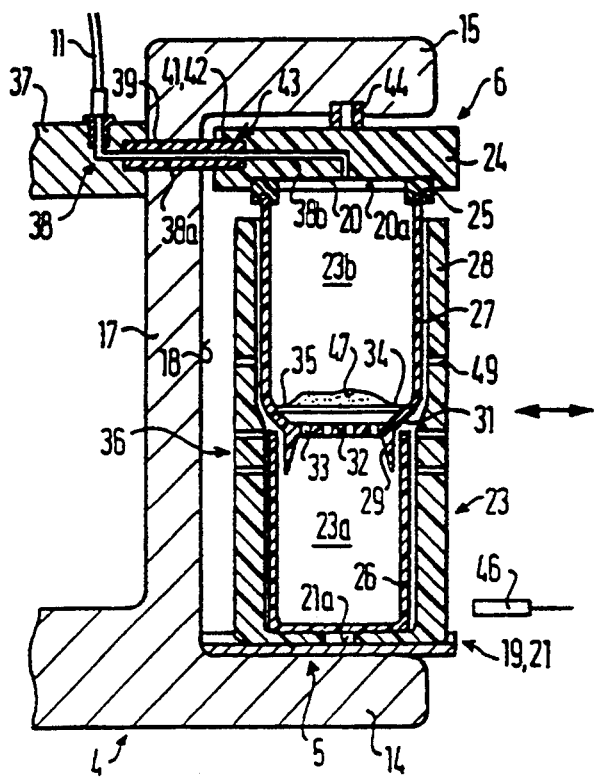
FIG. 2 a vertical partial section through a holder for one or more containers which is disposed in the heated area of the device.

The heating appliance 2 is integrated into a block-shaped housing 13, from the front of which the heating chamber 3 in the form of a block-shaped recess is accessible and is tightly closable by means of a sealing door which, for the sake of simplicity, is not shown. The suction line 9 and the supply line 11 open through associated openings into the heating chamber 3. The holder 4 is made of microwave-permeable material, in particular a plastic such as polypropylene, and is a rotating part having a bottom rotating plate 14 and a top rotating plate 15, between which the containers 6 are held. The rotating part may be driven in the sense of continuous rotation or alternatively a reciprocating swivelling movement, preferably through approximately 360°. The rotating plates 14, 15 are firmly connected to one another by a vertically extending connection part, here a connection tube 17 (FIG. 2), in such a way that they project out radially beyond the connection tube 17 (FIG. 2) and form between them a common annular recess 18 or individual recesses for receiving the containers 6. As shown in FIG. 2a guide 19 for the container 6 is preferably provided on the top of the bottom rotating plate 14 in the region of each positioning point 5 and positively effects a radially inward motional guidance when the container 6 is inserted laterally between the rotating plates 14, 15. The guide 19 may be formed by an indentation 21 with a flat bottom surface 21a, whose width extending in a peripheral direction is adapted to the width of the preferably cylindrical container 6.

As FIG. 2 particularly reveals, the identical containers 6 each comprise a pot-shaped part 23 and a flat lid 24, which rests on the top edge with the insertion of a ring seal 25 and may overlap the edge of the pot 23 slightly in a downward direction so as to be secured against lateral displacement. The underside extension 20 with a flat seating surface 20a for the edge of the pot 23 engages around said edge.

The pot 23 of the container 6 comprises a plurality of parts, in the present case three parts, namely a bottom pot part 26, a top pot part 27 sealed at its top edge, and a pot-shaped jacket 28 which may extend only as far as the top pot part 27 or substantially over the entire height of the container 6 and accommodates the pot parts 26, 27 with clearance of motion. There is preferably disposed, at the bottom end of the top pot part 27, a centering shoulder 29 which fits into the bottom pot part 26, the top pot part 27 resting with a shoulder 31 on the top edge of the bottom pot part 26. The base 32 of the top pot part 27 has a plurality of through holes 33 or is perforated in the manner of a sieve. Additionally associated with the top pot part 27 is a filter plate 34, preferably a so-called glass or paper filter, whose shape and size is such that it may be placed on an internal shoulder 35 of the top pot part 27. It is advantageous to provide a step or bevel in the region of the internal shoulder 35 so that, when the filter plate 34 is in place, there is a gap between it and the base 32. In the present embodiment, the individual parts of the containers 6 are circular or cylindrical in horizontal cross-section. To facilitate handling during insertion and removal of the pot parts 26, 27 into and out of the jacket 28, the latter may be divided by a horizontal dividing seam 36 into a bottom jacket part and a top jacket part. The container 6 is made of microwave-permeable material, in particular corrosion-proof plastic, preferably polytetra-fluoro-ethylene (PTFE Teflon) or tetrafluoro-copolymer (TFM) or the like. The pot parts 26, 27 or a single pot part may also be made of glass, quartz or ceramics. The individual parts of the container 6 and preferably the jacket 28 may also be formed from partially microwave-permeable material so that they are heated during radiation by the microwave generator (not shown), thereby preventing condensation and achieving residual heating after the microwave is switched off. A suitable material for said purpose is preferably a plastic in which material parts such as particles of microwave-absorbing material, in particular graphite, are incorporated or alloyed and which is known as Weflon.

The supply lines 11 extend from above at the centre of the holder 4 into the heating chamber 3 and are connected by connection fittings to a connection plate 37 inserted in such a way into the connection tube 17 that its peripheral surface rests against the inner peripheral surface of the connection tube 17. One angular channel 38 for each supply line 11 extends at first axially and then radially in the connection plate 37 and continues as a radial channel portion 38a in the connection tube 17. The channel portion 38a may be formed by a sleeve 39 which is firmly inserted into a bore provided in the connection tube 17, projects out beyond the connection tube 17 and hence forms a coupling or assembling pin 41. At its inner end, the sleeve 39 may also project into a corresponding bore of the connection plate 37, thereby fixing the latter in position. The sleeve 39 is preferably made of plastic. Said arrangement of the connection plate 37 is intended for a holder 4 which swivels back and forth.

Situated in the peripheral surface of the lid 24 is an insertion hole 42, whose shape and size are adapted to the shape and size of the assembling pin 41 so that the lid 24 with the radial insertion hole 42 may be mounted tightly onto the sleeve 39 and the assembling pin 41. The vertical clearance of the sleeve 39 from the bottom surface 21a is equal to the clearance of the insertion hole 42 from the underside of the container 6. Consequently, upon horizontal insertion of the container 6 into the associated positioning point 5, the line connection designated 43 may be simultaneously established by the horizontal insertion movement and severed upon removal in the opposite direction. Provided between the top of the lid 24 and the top rotating plate 15 and supported on one of said two parts is a spring part 44, preferably in the form of a vertically disposed, axially elastically compressible sleeve, which in the inserted position of the container 6 prestresses the lid 24 slightly towards the pot 23 and hence guarantees sealing of the lid 24. From the insertion hole 42, a channel, in particular an angular channel 38b, extends radially inwards in the lid 24 and preferably opens out in the centre at the underside of the lid 24 and hence into the cavity of the pot 23.

The suction line 9 is connected to the heating chamber 3 so that, when the device 1 is in operation, a partial vacuum may be generated in the heating chamber 3. Said partial vacuum may continue through the existing gaps or channels specially provided for said purpose, on the one hand, between the pot parts 26, 27 and the jacket 28 and, on the other hand, between the pot parts 26, 27 firstly into the bottom application chamber 23a and then also into the top application chamber 23b. Owing to the effect of said partial vacuum, the vapour arising in the containers 6 during treatment may be extracted, witch the treatment being accelerated owing to the passage of the vapour and/or solvent through the sample material situated on the filter 34 and/or the sieve plate 32.

Extraction of the vapour may be improved by admitting air or a gas into the heating chamber 3, thereby achieving an air or gas flow during extraction. This may be achieved through an aeration opening shown in FIG. 1 preferably by an aeration valve 40 which is disposed in a channel 40a in the housing 13, connects the heating chamber 3 to the environment, is preferably accessible from outside and is to be selectively opened and closed and is preferably adjustable. Owing to the gas or air stream which develops during extraction, the vaporous constituents may be extracted more efficiently, in the sense of being flushed, from the inner chamber of the container 6 and from the heating chamber 3.

Figure 3:
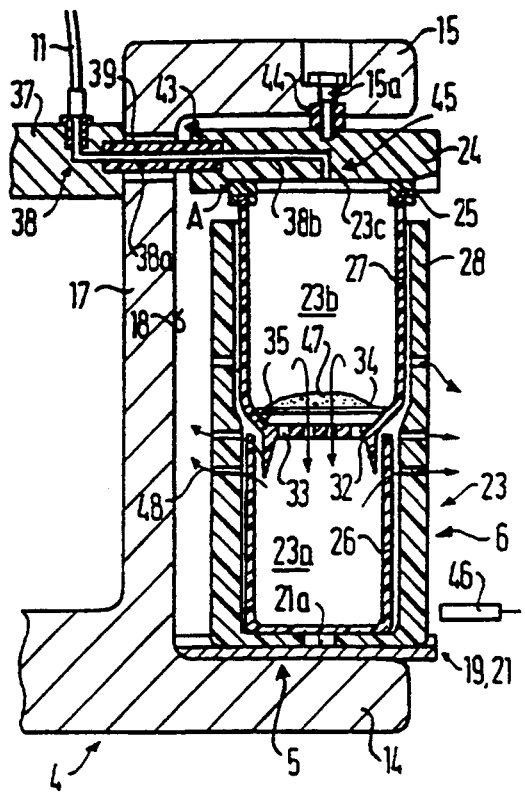
FIG. 3 a vertical partial section corresponding to FIG. 2, in a modified construction of the device.
Figure 4:
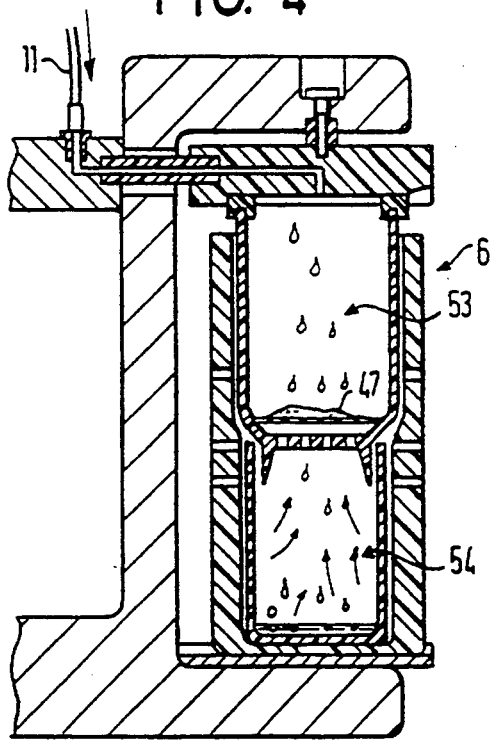
FIGS. 4 and 5 various operating states of the constructions according to FIG. 2 or 3.
Figure 5:
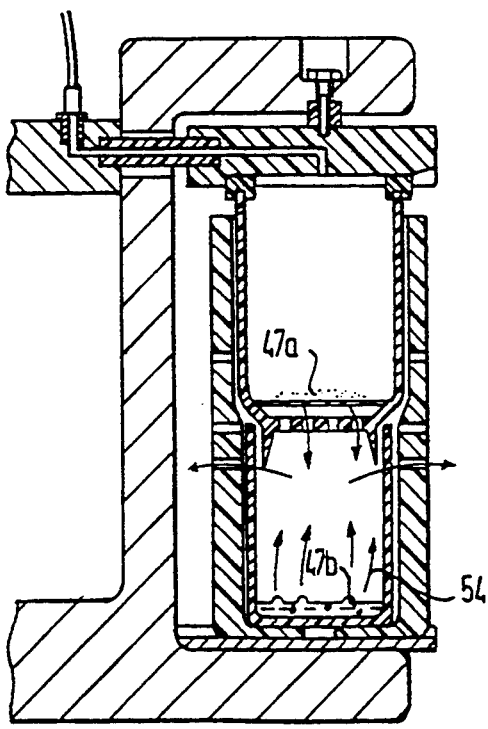

The embodiment according to FIGS. 3 to 5, in which identical or comparable parts are provided with the same reference numerals, differs from the embodiment according to FIG. 2 merely in that the lid 24 is disposed or held on the holder 4 and so is part of the holder 4. For holding the lid 24 on the holder 4, a locking screw 15a is used, which fits through a vertical hole disposed in the top rotating plate 15 preferably coaxially to the container 6 and is screwed into a threaded hole in the top of the lid 24, the locking screw 15a vertically penetrating the sleeve-shaped spring part 44. By means of the locking screw 15a, whose head is preferably countersunk in the top of the top rotating plate 15, the lid 24 may not only be held but its height may also be adjusted by screwing the locking screw in or out. The lid 24 is additionally resiliently held at its inside by the plug-in connection 43, this being achievable by a radial clearance of motion of the sleeve 39 in the connection tube 17 in addition to the flexibility of the sleeve 39. In said construction, the plug-in connection 43 is designed for a continuous connection. Since the lid 24 is held on the holder 4, for insertion and removal of the container 6 only the pot 23 is inserted into and removed from the positioning point 5. During said process, the pot 23 is not only automatically closed and opened but a line connection 45, provided instead of the plug-in connection 43, between the supply line 11 and the top application chamber 23b of the pot 23 is also established upon insertion and severed upon removal. Said line connection 45 is formed by the channel 38b and the opening 23c of the pot 23. Unlike the construction according to FIG. 2, in which the axis of the plug-in connection 43 extends horizontally, the axis of the line connection 45 extends vertically.

In the construction according to FIG. 3, moreover, the lid 24 is set at such a height that the pot 23 may be inserted with a slight vertical clamping action between the lid 24 and the bottom rotating plate 14, which rotating plate may be provided with a special guide part comprising the guide 21. Since the locking screw 15a is not restricted in an upward direction, upon insertion of the pot 23 the lid 24 may be pressed slightly upwards against the spring action of the spring part 44. To facilitate insertion, lead-in bevels may be disposed externally on the underside of the lid 24 and/or internally on the top of the lid 24.

In the present construction according to FIG. 3, the recess 23c in the underside of the lid 24 is open in a radially outward direction so that the pot 23 may be inserted laterally into the recess 23c. The radially inner boundary surface of the recess 23c forms a stop A, which cooperates with the top edge of the pot 23 or the ring seal 25 and delimits the insertion movement of the pot 23 in the desired upright position. Thus, the recess 23c also forms an insertion guide 19.

Associated with the device 1 is a device for measuring the temperature in or at the containers 6. Said device is preferably at least one non-contact thermometer, in particular an infrared thermometer 46, which is preferably disposed in the bottom region of the plane of rotation of the containers 6 laterally of the holder 4 and past which the containers 6 travel during operation. The thermometer 46 is connected by an electric control line to the control device 12 (FIG. 1).

An evaporation process is described below with reference to FIGS. 2 to 5. The intention is, for example, to determine the moisture or fat content of a material sample 47. To said end, an amount of the sample 47 is applied onto the filter plate 34 and weighed by means of the balance 10 to determine its quantity. The filter plate 34 carrying the sample 47 is then inserted into the top pot part 27, with the pot parts 26, 27 possibly being already situated in the jacket 28 or being subsequently inserted therein. The container 6 with lid 24 (FIG. 2) or without lid 24 (FIG. 3) is then inserted horizontally into its treatment position on the associated positioning point 5, thereby automatically establishing the line connection 43 or 45. Owing to the tension of the spring part 44, the lid 24 is tightly closed, with the sample 47 being situated in the bottom region of the top pot part 27 on the filter plate 34 (FIG. 2 and 3). The evaporation process may then begin. The heating appliance 2, the holder 4 and the suction pump 7 may start simultaneously, and the suction pump may generate a pressure of 20 mbar and the heating appliance 2 may generate a temperature of around 80° C. in the heating chamber 3. Said treatment period may last about 5 minutes. During said period the sample is dried, with any moisture content in the sample being volatized and extracted, this being illustrated by the flow arrows 48 shown in FIG. 3. The volatile fractions pass out of the top application chamber 23b through the filter plate 34 and the perforated base 32 into the bottom application chamber 23a and, from there, through the above-described gaps or special radial through holes 49 in the jacket 28 or bottom jacket part 28a and/or top jacket part 28b into the heating chamber 3, and they are further extracted by the suction line 9, condensed in the cooler 8 and collected. By said means the sample 47 is dried. If only drying is to be achieved, the treatment of the sample may then be regarded as already complete. The level and duration of the temperature in the heating chamber 3 may be determined by a time switch and/or the thermometer 46, which measures the temperature at or in the container 6. After the treatment stage described above, the partial vacuum in the heating chamber 3 may be reduced, this being possible by opening the valve 40 in the wall of the heating chamber 3. The valve 40, too, may be selectively opened and closed automatically by the control device 12.

A next treatment step may be effected according to FIG. 4 under normal pressure in the heating chamber 3. By means of a pump (not shown) or gravity, a specific quantity of the solvent 53 (eluent), e.g. about 10 ml, is admitted preferably into the centre of the top application chamber 23b so that the solvent 53 passes onto the sample 47. At the same time, the heating appliance 2, the suction pump 4 and the holder 4 are switched on or driven and a small quantity of solvent, around 3–5 ml, may additionally be introduced. The hot solvent 53 runs through the sample 47 and the filter 34, passes already in the process of evaporation into the bottom application chamber 23a and is further evaporated there (arrows 54) and extracted from the system in the manner described.

The solvent vapour may be condensed and reclaimed in the condensation cooler 8. Recycling through specially provided return lines is also possible (not shown). During said treatment step, the passage of the solvent 53 with possibly already existing vapour fractions through the filter 34 and the base 32 is accelerated by the partial vacuum. With said treatment step too, the treatment period may be determined or controlled by the treatment time and/or temperature.

In the next treatment step according to FIG. 5, total drying may—if desired—be effected. The solvent 53 then completely evaporates, and the temperature may be maintained by suitable control of the heating appliance or the heating appliance may be switched off. This is possible because the temperature in the jacket 28 reaches its maximum and brings about a residual heating effect and hence the drying. Operation of the suction pump may be maintained up to the end of the treatment step. The partial vacuum may also be reduced by opening the valve 52. After said treatment step, a residue 47a of the sample material is situated on the filter 34. Fat eluted from the sample material (eluate) 47b is situated on the bottom of the bottom pot part 26. By weighing the fat and the residue, the desired test values may be determined.

In the condensation cooler 8, which is also subject to the suction action of the suction pump 7, the solvent vapour may be condensed and reclaimed. By means of a line (not shown), the condensation product may be returned to the supply line 11 and recycled.

In the embodiments according to FIGS. 1 to 5, external cooling of the holder 4 and the containers 6 is also effected by means of the gas or air stream traversing the heating chamber 3.

The embodiment according to FIGS. 6 to 8, in which identical or comparable parts are provided with the same reference numerals, is distinguished from the embodiment described above by a plurality of alternatives. Firstly, the containers 6 are each disposed in their own partial-vacuum chamber 61 which is formed by an, in particular, hollow cylindrical wall horizontally surrounding the associated container 6 with a slight clearance, or by a pot-shaped, preferably likewise hollow cylindrical housing 62, with the peripheral wall which forms the partial-vacuum chamber 61 tightly cooperating at its top edge with the lid. Each partial-vacuum chamber 61 is connected by a suction line 63 to the suction pump 7, the suction line 63—in a comparable manner to the supply line 11—possibly branching off from the common suction line 63 in a distributor or branch piece 64 into as many lines leading to containers 6 as there are containers. The common suction line 63 is preferably connected axially by means of suitable connection fittings to the central distributor piece 64, whose downward extending through channel 66 opens into a clearance 67, which is disposed below the distributor piece 65 and from which the desired number of suction line portions 63a may branch. Said holder 4 is therefore geared for continuous rotation. The reagent is introduced into the container or containers prior to insertion of the latter.

As far as support of the lid 24 is concerned, the lid is held on the holder 4 as in the embodiment according to FIG. 3 by the locking screw 15a and the plug-in line connection 43, with the pot 23, which in the present case forms a unit with the partial-vacuum housing 62, being insertable between the lid 24 and the bottom rotating plate 14 and removable horizontally from the side, and the lateral guide 19 may here be formed by the recess 20 in the underside of the lid 24.

Here too, the line or plug-in connection 43 is formed by the sleeve 39 which communicates with the clearance 67. The channel 38b does not however open out from the centre of the container 6 at the underside of the lid but opens into the gap between the pot 23 and the partial-vacuum housing 62, said gap being only about 1 mm or a few millimetres wide. Since the volume of the partial-vacuum chambers 61 is therefore low, less power is required to generate the partial vacuum.

If an automatic supply of reagent or solvent 53 is desired, a supply line 11a may be provided, which may be connected by a suitable fitting to a through channel 68 preferably extending from top to bottom in the lid 24, the through channel 68 preferably opening into the pot 23 at its centre. In the construction according to FIG. 7, an additional flat lid 24a is provided, which is disposed on an internal shoulder 23d in the top edge region of the pot 23, preferably recessed in the latter. The arrangement may be effected in such a way that the lid 24a rests flat against the underside of the lid 24 oar the seating surface 20a of the recess 20. The additional lid 24a is preferably likewise made of a material, in particular plastic, which resists the microwaves in such a way that it is heated during operation (Weflon). The reagent or solvent 53 passes through a vertical central hole 24b in the bottom lid 24a into the pot 23. The reagent supply lines 11a may comprise separate lines or branch lines emanating from, a common line, which are connected to a feed pump 60. On account of the supply line or lines 11a, said holder 4 is rotated back and forth during operation.

Said construction, too, is provided with an aeration valve 40, which may be disposed in the region of the suction pump 7 and as a sweeping valve in the lid 24 and whose aeration channel 40b and/or 40c may be connected to the partial-vacuum chamber 61 and/or the inner chamber of the pot 23 in the manner indicated in FIG. 7.

The supply lines 11a may extend through holes 15b disposed in the top rotating plate 15.

A further distinguishing feature of the construction according to FIGS. 6 to 12 is that the top pot part 27 rests with an external flange 27a on the top edge of the partial-vacuum housing 62, which may likewise have an external flange. The top pot part 27 is centered in the partial-vacuum housing 62 by means of an annular shoulder 27b which is disposed on the underside of the flange 27 and fits with clearance of motion in the partial-vacuum housing. The annular gap between the pot 23 and the partial-vacuum housing 62 is situated below the annular shoulder 27b. Further provided is the bottom pot part 26 which, from below, overlaps the bottom end of the top pot part 27 and may thereby be centered. It is advantageous to place on the bottom of the bottom pot part 26 a tray 26a, on which residues of the sample material may collect and then be easily removed. The passage between the channel 38b and the partial-vacuum chamber ,51 is effected by a vertical channel 27c, which vertically penetrates the flange 27a and the annular shoulder 27b and is aligned with the channel 38a. When an annular groove communicating with the channel 38a is provided at the underside of the lid 24 or at the top of the flange 27a, the channel 27c need not be in alignment.

In the pot 23 according to FIGS. 7 to 12, the jacket 28 is situated in the partial-vacuum chamber 61 and may lie with its external lateral surface against the partial-vacuum housing 62 or preferably with its internal lateral surface against the bottom pot part 26. In all of the embodiments, the jacket 28 may be a pot-shaped housing, i.e. have a base 28a which extends below the pot 23 and preferably has a hole 28b in its centre.

The device 1 of said embodiment operates in a similar manner to the embodiment described above, except that the heating chamber 3 is not directly evacuated but only the respectively associated partial-vacuum chamber 61, this being effected by means of the suction pump 7 and the suction line 63, 63a. In other words, the free heating chamber 3 is released from conduction of the extracted vapours. There is however an air or gas flow between the aeration opening 40a and the aeration channels 40b. As a result, the constituents of the solvent and possibly of the sample material which evaporate under microwave radiation are extracted firstly out of the top application chamber 23b into the bottom application chamber 23a and then through seams or gaps provided between the bottom pot part 26 and the top pot part 27 into the partial-vacuum chamber 61 and on from there. In said embodiment too, the vapour may be condensed in the cooler 8, reclaimed and recycled as solvent.

The embodiment according to FIG. 13, in which identical or comparable parts are likewise provided with the same reference numerals, differs from the embodiment according to FIG. 7 in that the container 6 is of a different construction and there is a different application, namely to purify a solvent by evaporating it, the impurities being left on the base of the pot 23. In the course of evaporation the solvent is supplied, while being simultaneously heated by means of microwaves, through the supply line 11a, with at the same time the suction pump and the rotary operating mechanism being switched on so as to generate in the partial-vacuum chamber 61 surrounding the, in this case single-piece, pot 23 a partial vacuum which continues through radial holes 23d in the top half or in the top region of the pot 23 into the inner chamber 23e of the pot, so that the solvent vapour is extracted. Here too, the aeration valve 40 may improve a desired sweeping function. In order to increase the retention time of the solvent passing into the inner chamber 23e before it reaches the base of the pot 23, there is disposed in the pot 23 a downward spiralling conduit 82, into which the liquid solvent drops from the through hole 76 and flows helically downwards. The prolonged travel in the conduit 82 results in the desired increase in the exposure time during which the microwaves may heat and evaporate the solvent.

Figure 14:
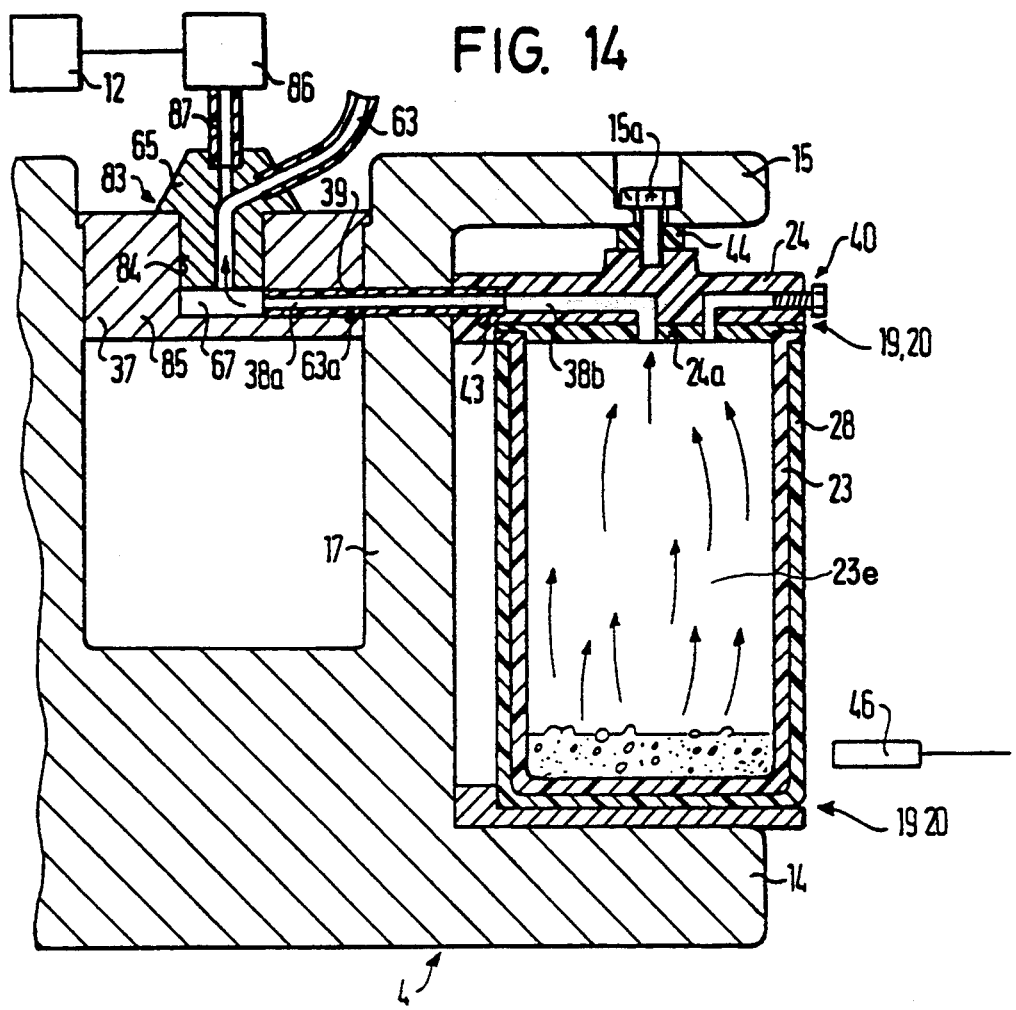

In the variant of the device 1 according to FIG. 14, in which identical or comparable parts are likewise provided with the same reference numerals and, to avoid repetition, are not further described, a single-piece pot 23 is likewise provided which may be horizontally inserted into and removed from its operating position between the bottom rotating plate 14 and the lid 24 held on the holder 4. Said construction is likewise provided with a line 63a extending through the lid 24, the plug-in connection 43 and the distributor piece 65, but said line is not a supply line but a suction line which is possibly connected to the condensation cooler 8 and the suction pump 7.

In said construction, the sample material and/or solvent is introduced into the container 6 before the pot 23 is inserted into the holder 4. In the course of heating and evaporation, evaporable constituents of the sample material and/or solvent are evaporated and the vapours are extracted upwards through the suction line 9a, the aeration valve 40 provided in the lid 24 effecting an advantageous sweeping of the inner chamber 23e of the pot 23.

In the construction according to FIG. 14, the distributor piece 65 is part of a revolving joint 83 which, given continuous rotation of the holder 4, enables a simultaneous distribution and bringing together of the channels 38a of the containers 6 to form the common suction line 63, the distributor piece 65 remaining stationary in the pivot bearing hole 84 of a pivot bearing piece 85, which is inserted into the connection tube 17 and rotates with the holder 4 about the distributor piece 65. The bringing together of the streams is effected in the clearance 67 below the distributor piece 65 or the latter's through channel.

Figure 15:
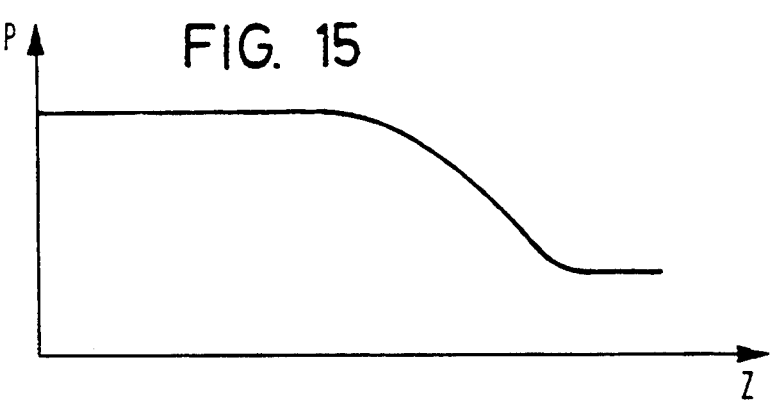
FIG. 15 an operational diagram from which the temperature curve can be seen.

According to FIG. 14, there is associated with the device 1 a device for measuring the partial vacuum in the container 6, which device is connected by its electric control line to the control unit 12 and so enables control or regulation of the heating appliance 2 as a function of the partial vacuum. In the present construction, a vacuum gauge 86 is provided, which is connected by a pipe or tube 87 to the suction line 63—and so gives a partial-vacuum reading roughly corresponding to the partial vacuum in the container 6—and is connected to the control device 12, which with the aid of an evaluation device is designed so as to supply a control signal when the partial vacuum falls below a preselected value. Said construction enables an advantageous procedure for determining the end point of evaporation. When the evaporable constituents have been evaporated and evaporation ceases, the suction pressure generated by the suction pump 7 (FIG. 2) automatically drops because the uniformly operating suction pump 7 generates a greater partial vacuum in the absence of evaporation. By said means, the end point of evaporation is determined and the treatment process is brought to an end by switching off the device 1 or the suction pump 7, the heating appliance 2 and the rotary operating mechanism for the holder 4, with the aeration valve 40 also possibly being opened to establish normal pressure. FIG. 15 shows the pressure characteristic with a pressure drop as a curve, with time Z being plotted on the X-axis and pressure P on the Y-axis.

An alternative method of determining the end point of evaporation is by taking into account the temperature characteristic in the container 6. The control device 12 is designed to produce a control signal in the event of a temperature rise above a predetermined level or a temperature rise which is occurring faster than normal. When the evaporable constituents in the container have been evaporated and evaporation therefore ceases, heating energy is no longer consumed for evaporation, this automatically leading to a temperature rise. By said means, the end point of evaporation is determined and the device produces the control signal described above, as a result of which the evaporation process is brought to an end, i.e. the device 1 is switched off in the manner described above.

Figure 16:
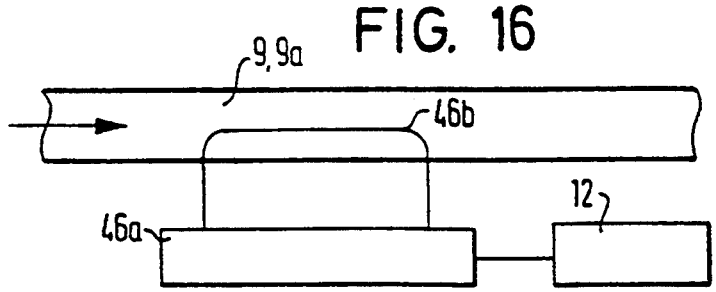
FIG. 16 a diagrammatic view of a device for measuring the vapour temperature.
Figure 17:
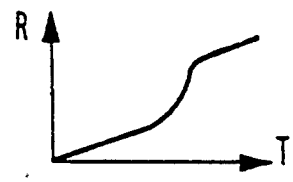
FIG. 17 an operational diagram from which the temperature curve can be seen.

The thermometer 46 may be used to monitor and measure the temperature. It is even more advantageous to measure the temperature directly in the suction line. To said end, according to FIG. 16 a thermometer 46a with a resistor or resistance wire 46b may be used, which measures the temperature directly in the suction line 63 or associated channel portions. As the temperature rises, the resistance value increases so that the temperature characteristic and the temperature may be electrically monitored and measured. The thermometer 46a is also connected by an electric signal line to the control device 12 which, if the temperature rises beyond a predetermined amount, produces the control signal described above for bringing the evaporation process to an end. FIG. 17 shows the temperature characteristic with a temperature rise as a curve, the temperature T being plotted along the X-axis and the resistance R being plotted along the Y-axis.

In the embodiments according to FIGS. 7 to 17, an external cooling of the holder 4 and the containers 6 and also an internal cooling of the containers 6 is effected by the gas or air stream.

Figure 18:
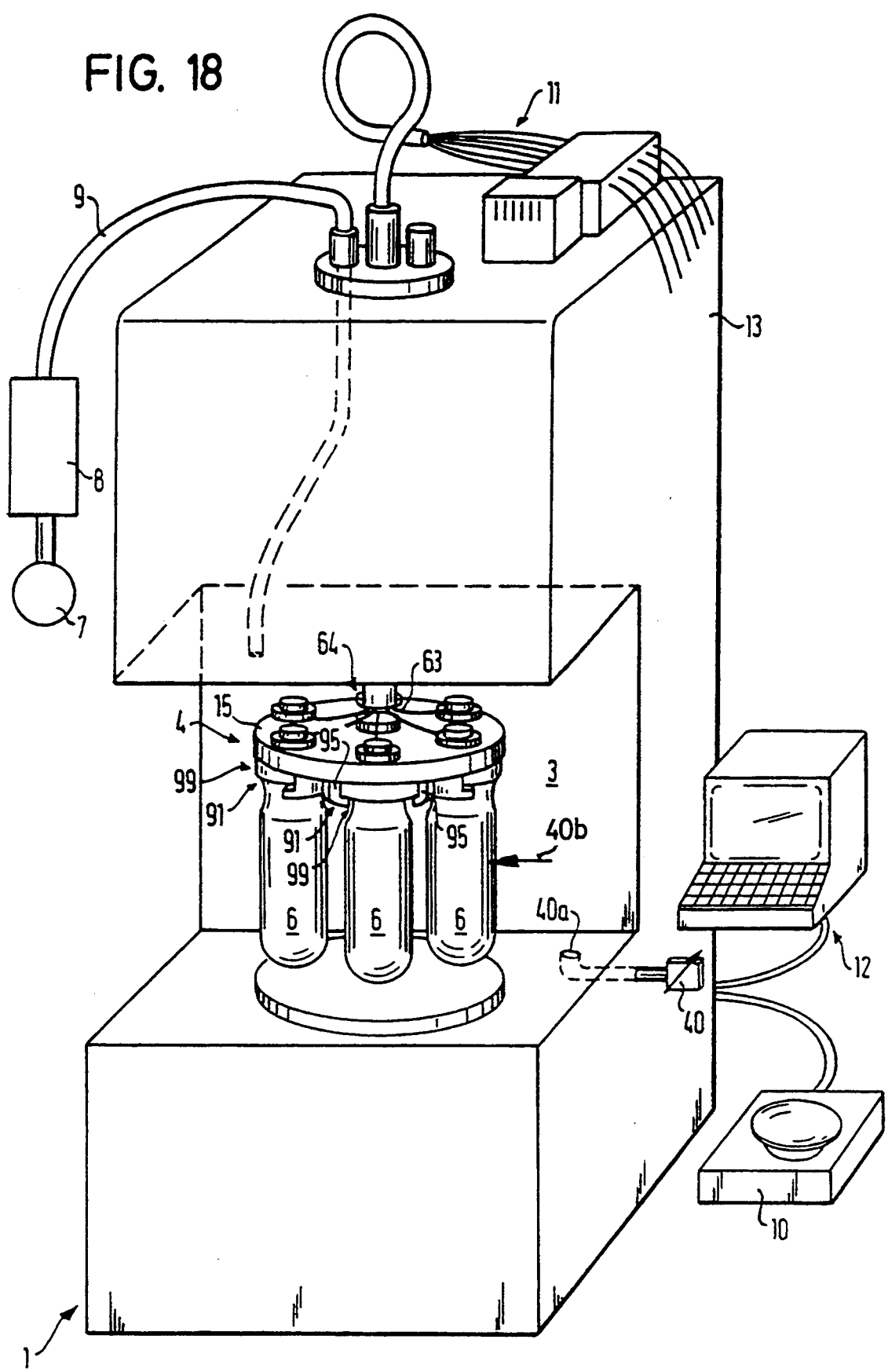
FIG. 18 a perspective view of a further modified construction of a device according to the invention for evaporating in particular liquid substances, preferably with reagents, or for preparing or analysing sample material.
Figure 19:
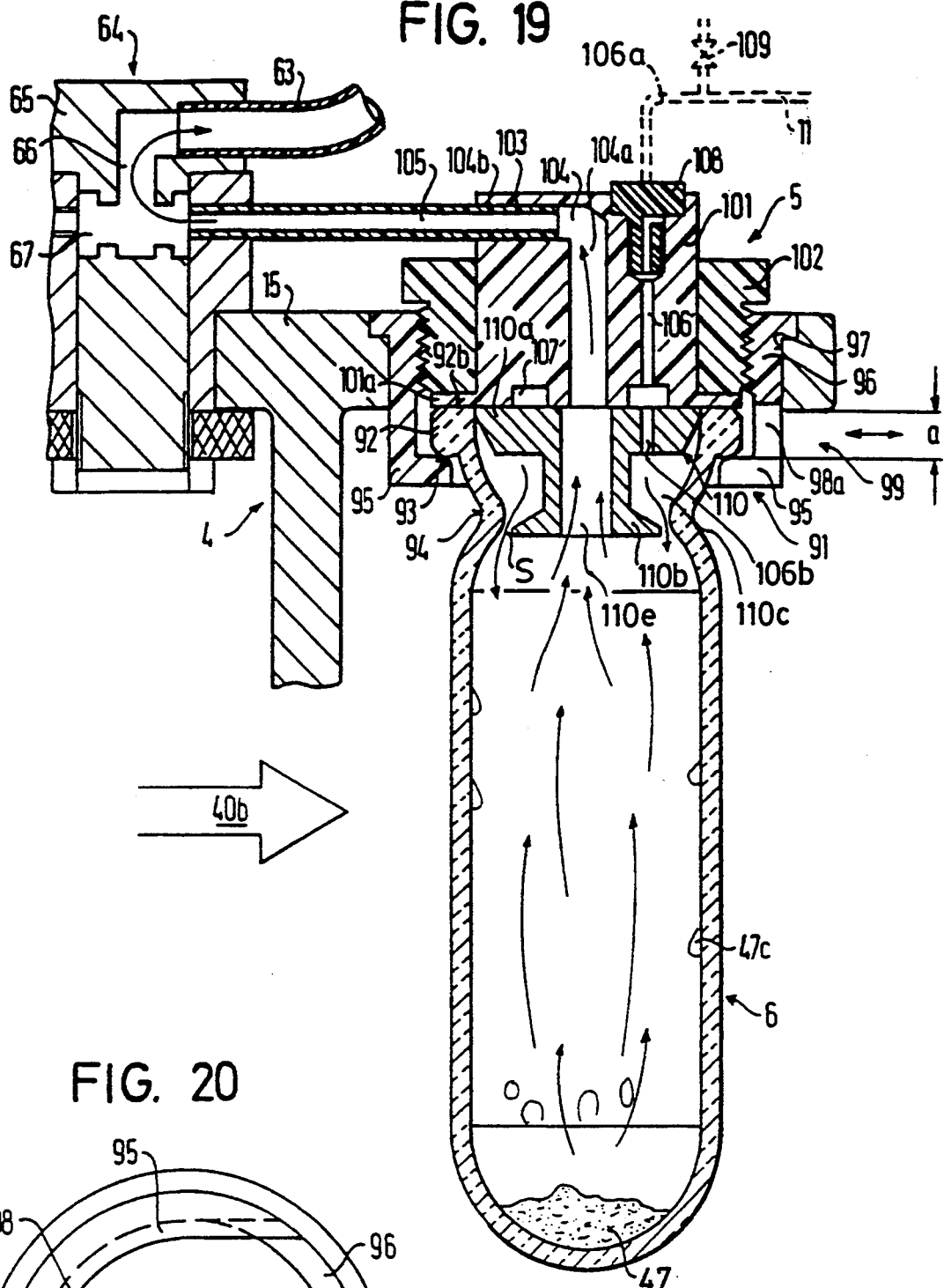
FIG. 19 a vertical partial section through a holder having a container fastened thereto.
Figure 20:
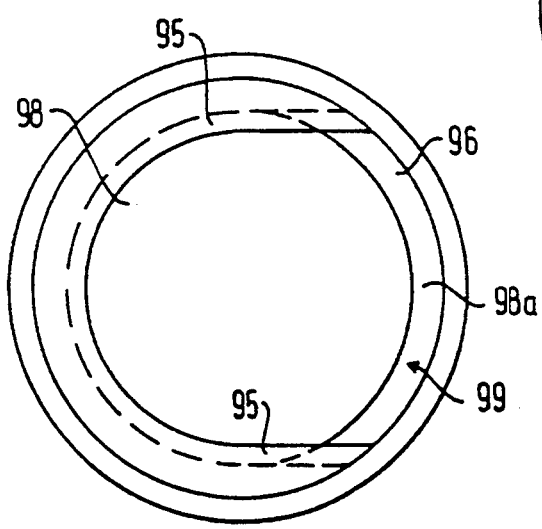
FIG. 20 a view from below of a holding element of the holder.

The construction according to FIGS. 18 to 20, in which identical or comparable parts are provided with the same reference numerals, differs from the constructions described above in two respects. Firstly, the containers 6 are each held in a suspended position in the holder 4 by means of a suspension device 91 and, secondly, an air-sweeping device for the heating chamber 3 is provided which substantially corresponds to the extraction device formed by the suction pump 7, the suction line 9 and the aeration valve 40 but is used, not to extract vapours, but to circulate cooling air.

Given a suspended support of the containers 6, the holder 4 is easier and less expensive to manufacture because it is possible to dispense with the bottom rotating plate 14. Given such a construction, the respective positioning point 5 is provided only on the top rotating plate 15 of the holder 4 which, apart from this, may correspond to the construction of the holder 4 according to the embodiments described above.

With said construction, containers 6 are used which have suspension shoulders disposed some way down from their top edge. In the present construction, the containers 6 have at their top edge a horizontal edge flange 92 (FIG. 19) with a lower surface 93, over and under which holding parts of the suspension device 91 engage. The present containers 6 have, below the edge flange 92, a neck-like constriction 94 which is formed by a peripheral bead of the upright container wall, so that the inner chamber of the container is also constricted in the region of the neck-like constriction 94. For suspending the containers 6, two lateral angled limbs 95 disposed on the underside of the top rotating plate 15 may be used, which laterally engage over and under the edge flange 92.

In the present construction, the angled limbs 95 are formed by the bottom edge of a cylindrical bush 96, which is inserted in a vertical bore 97 in the top rotating plate 15 and is locked by means of a flange against vertical displacement and against rotation e.g. in a form-fit manner or by means of an interference fit or gluing. As FIG. 20 particularly reveals, the bottom of the bush 96 is relieved by a circular recess 98, which is open in a radially outward direction and extends to this side as far as into the bottom region 98a of the peripheral wall of the bush 96, thereby forming a lateral radial insertion opening 99 for the edge flange 92, into which opening the edge flange may be inserted with clearance of motion (see double arrow). To said end, the vertical clearance a between the underside of the rotating plate 15 and the supporting surface of the angled limb 95 is made slightly greater than the thickness of the edge flange 92.

The surface 92b of the edge flange 92 may rest particularly tightly against the underside of the holder 4 or, in this case, the rotating plate 15. In said region, a stopper 101 is preferably disposed in the holder 4 and may be clamped against the edge flange 92, thereby establishing or improving sealing and securing the container (6). In the present construction, the stopper 101, which is circular in cross-section, is rotatably supported with slight clearance of motion in a threaded retaining ring 102, which may be screwed from above into the bush 96 and has, at its top end region projecting from the bush 96, application elements for enabling it to be screwed in and out by hand or by a tool. The stopper 101 is made longer than the threaded retaining ring 102 and engages below the latter with a flange 101a at its bottom end, with its top end projecting about 5 to 10 mm beyond the threaded retaining ring 102. Said projecting end region is designated 103. Situated in the stopper 101 is a through channel 104 comprising a preferably coaxial channel portion, which opens out at the underside, and a radial channel portion which opens out of the stopper 101 in the end region 103. The radial channel portion 104b is connected by a line connection extending above the rotating plate 15, e.g. a firmly attached tube or pipe, to a revolving joint 64 substantially corresponding to the embodiments described above, to which the discharge line portions 105 lead and are connected to a common discharge line 63.

Provided off-centre in the stopper 101 is a further through channel 106 which is part of an aeration device for the container 6. The through channel 106 opens at the underside of the stopper 101 into an annular groove 107. At the top end of the stopper 101, a valve screw 108 may be screwed into the stopper and the through channel 106 may, by screwing said valve screw in and out, be selectively closed, opened and adjusted in size. For said purpose it is also possible to provide a suitable valve 109 which is disposed in a tube or pipe 106a externally connected to the through channel 106. Between the stopper 101 and the valve 109, the line 106a may branch in the form of a supply line 11, especially for the purpose of supplying a reagent, e.g. by means of a pump.

Preferably disposed in the top opening region of the container 6 is a stopper-like baffle element 110, whose top surface is level with the top surface 92b of the edge flange 92 and so lies—as the container 6 already does—sealingly against the underside of the stopper 101. The baffle element 110 comprises, coaxially, a lid 110a and a baffle head 110b extending down from the lid in the shape of a mushroom cap, said baffle head extending in the present construction roughly as far as into the neck-like constriction 94 and its diameter being so dimensioned as to form between it and the inner peripheral wall of the container 6 a small annular gap S. Between the baffle head 110b and the plate-like lid 110a there is a free annular chamber 110c. The lid 110a lies in a form-fit manner against the diverging wall of the edge region of the container 6 so that it is locked in position. Provided in the lid 110a in alignment with the annular groove 107, is a through channel 106b which, irrespective of the rotational position of the baffle element 110 at any one time, enables a throughflow of air or a specific gas, e.g. inert gas or reagent. A second larger through channel 110e, which is part of the discharge line portion 105, is provided coaxially in the baffle element 110 and hence in alignment with the through channel 104a.

The embodiment according to FIGS. 18 to 20 may operate in substantially the same manner as the embodiments described above so there is no need for a separate description. To effect an evaporation process or decompose a sample, the containers 6, which are preferably standard containers made of glass, quartz or ceramics, are after introduction of a sample material 47 inserted horizontally into the suspension device 91 and sealed, i.e. closed and simultaneously clamped, by screwing down the threaded retaining ring 102. Owing to said tight closure, the present construction is suitable for treating substances not only under normal pressure or a partial vacuum but also under excess pressure, for which purpose the threaded retaining ring 102 is to be accordingly closed. Instead of the screw-type bracing, a, in particular elastic, clamping device may be provided for prestressing the stopper 101 forming a lid towards the container edge.

In the course of the treatment process, the resultant vapours may be extracted through the discharge line 63, in which case at the same time the valve 109 (if provided) and/or the valve screw 108 is to be opened. Reagent may optionally be purposefully supplied through the supply line 11. During the treatment process, the containers 6 may be cooled by the sweeping air stream 40b also at their underside, so that a large surface area is cooled, said cooling being effected by sweeping the heating chamber 3 with the air which is extracted through the suction line 9 and is discharged at the supply opening 40, 40a. The vapour may condense on the inner wall of the container and run back down as condensation product 47c.

In all of the embodiments described above, it is possible and advantageous to effect the above-described treatments of a substance in at least one container 6 with the reagent or solvent in two or more stages, with there being at least partial use in each subsequent stage of a reagent or solvent which has been reclaimed from the preceding stage of treatment and has possibly been enriched with new reagent or solvent. According to Nernst's distribution law, the efficiency of extraction is greater when it is effected in stages than when a single longer extraction is effected. The consumption of solvent is also reduced.

Figure 21:
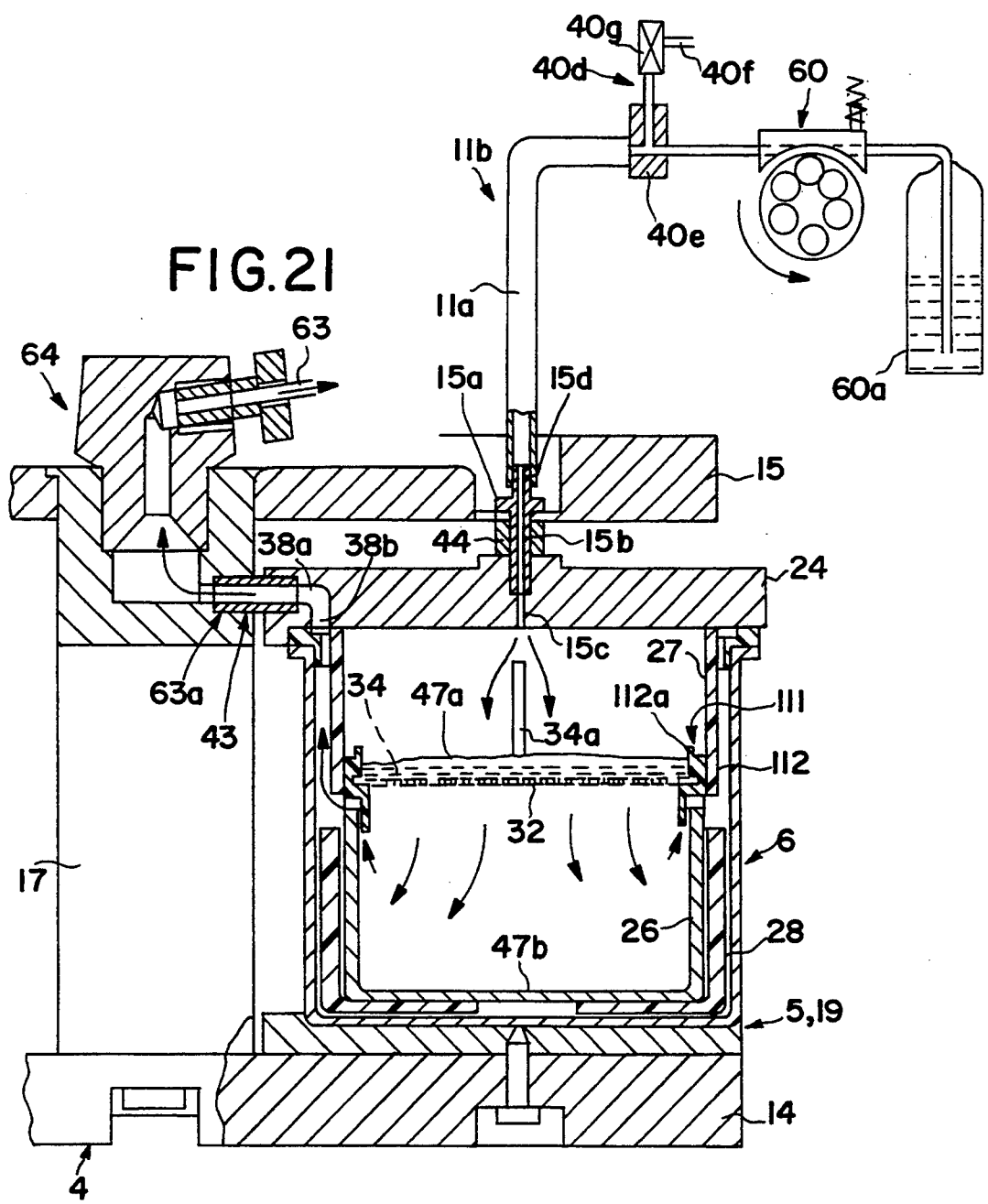
FIG. 21 a vertical partial section of a further modified construction of the holder for one or more containers disposed in the heated area of the device.

The embodiment according to FIG. 21, in which identical or comparable parts are provided with the same reference numerals, differs from the above-described embodiments having a supply device for a reagent or solvent and an aeration device for the container 6 in two respects.

Figure 22:
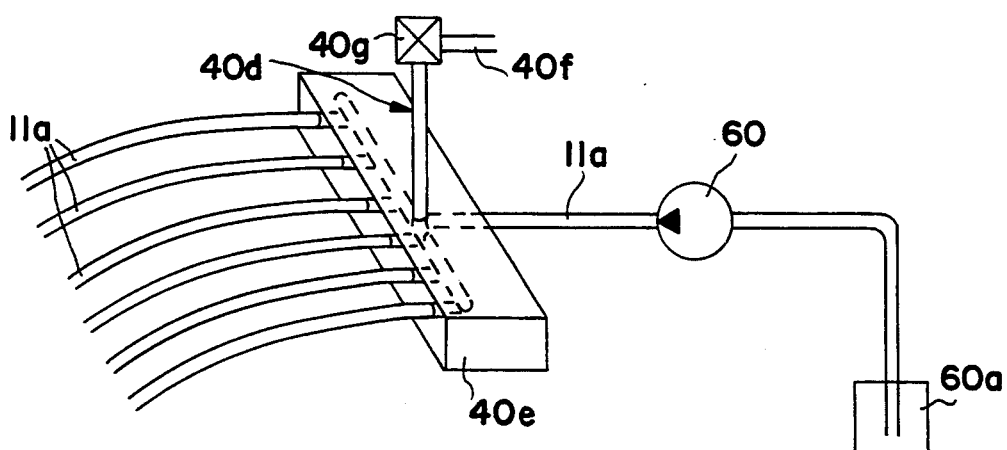
FIG. 22 a solvent- and gas-supply device according to FIG. 21 in a modified construction.

Firstly, the aeration device designated 40d in FIG. 21 is integrated into the supply device 11b. This makes it possible to utilize the supply line 11a both to supply the reagent and to aerate or sweep the associated container 6, so that there is no need for a separate aeration channel 40b, 40c, such as shown in FIG. 7, in the lid 24. According to FIG. 21, a branch line 40f, here a flexible plastic tube, opens inside a block 40e into the supply line 11a, which branch line emanates from the aeration valve 40 and may supply an aeration gas via a controllable non-return valve 40g. The branch line is disposed downstream of the pump 8 (FIGS. 1, 6 and 18)—here, a hose pump—so that the supply of aeration gas is guaranteed even when the pump 8 is not operating and no reagent is being supplied. The block 40e is disposed outside of the heating chamber 3 or it may alternatively be disposed in the heating chamber 3 provided that it and its add-on parts are made of microwave-permeable material. The flexible supply line 11a is made long enough to allow the holder 4 during operation to execute reciprocating swivelling movements. One storage container 60a and one feed pump 60 for each container 6 may be disposed preferably outside of the housing for the heating chamber 3, or a common storage container 60a and a common pump 60 may preferably be provided, the supply line 11a branching off in the block 40e into supply branch lines 11a, whose number corresponds to the number of containers 6 and which are each connected to the associated container after penetrating the top rotating plate 15 and the lid 24 (FIG. 22).

In the present embodiment, the supply line 11a in each case extends longitudinally through the associated locking screw 15a and does so in the form of a longitudinal channel 15b, to which a coaxial channel 15c in the lid 24 is connected, said coaxial channel opening out at the underside of the lid. At its top end, each locking screw 15 has a hose coupling—in the present case, a connection fitting 15d—onto which the associated supply line 11a is placed.

A further constructional difference relates to the fact that the formation of condensation product is prevented or that condensation product forming in particular in the top region of the container is collected and so is prevented from flowing down onto the sample residue 47b situated on the bottom of the container 6 and corrupting analysis of the sample residue 47b.

To prevent the formation of condensation product, an additional heating of the wall of the container 6 is provided. For said purpose, wall portions may be used which are made of microwave-absorbing material, preferably Weflon, with the container 6 itself possibly being made of such a material or being surrounded externally and/or internally by such a material. For said purpose, it is possible, for example, for the container 6 to be inserted into a cylindrical or pot-shaped jacket 28 of the type already illustrated in FIG. 7. In the case of a container 6 having a bottom part 26 and a top part 27, the jacket 28 extends only as far as the top region of the bottom part 26. A comparable jacket may also be associated with the top part 27.

A collecting groove 111 is provided on the inner periphery of the container 6 for collecting condensation product as it forms. The collecting groove 111 is situated above the bottom of the container 6. It may be moulded on the container 6 or be formed on an insertion ring, which is inserted into the container 6 and rests tightly against the inner wall to which it may be fastened. The collecting groove 111 may also be disposed above, the perforated base 32 so that the condensation product cannot reach the first sample residue 47a. In the case of a container 6 comprising a bottom part 26 and a top part 27, the collecting groove 111 may be disposed at the bottom end of the top part 27 and, according to FIG. 21, it may be integrally constructed with the sieve plate 32 or a carrier for said sieve plate or may form a structural unit therewith, the collecting groove 111 and the perforated plate 32 possibly being formed or carried by the insertion ring 112 which may rest on an internal shoulder at the bottom end of the top part 27 or on the edge of the bottom part 26. In the present embodiment, the collecting groove 111 is formed by a top annular projection 112a, which projects up from the insert ring 112 at a radially inward distance from the inner wall of the container 6. The sieve plate 32 may rest on a further shoulder of the insertion ring 112. The collecting groove 111 is preferably made of a microwave-absorbing material, in particular a plastic such as Weflon, and is preferably integrally constructed with its carrier.

Figure 23:
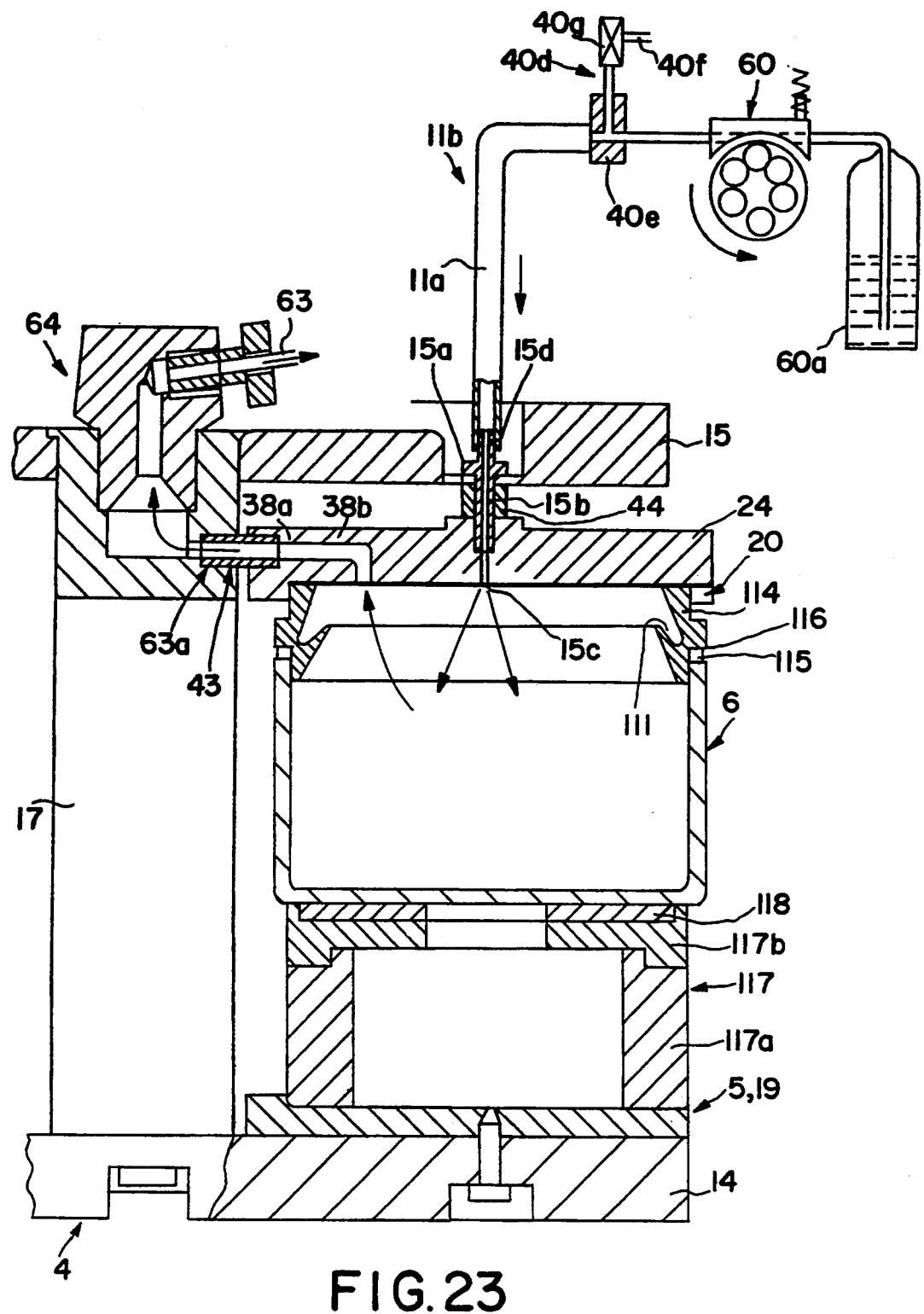
FIG. 23 a vertical partial section of the holder for one or more containers disposed in the heated area of the device, in a further modified construction.

In the embodiment according to FIG. 23, in which identical or comparable parts are likewise provided with the same reference numerals, the collecting groove 111 is disposed as a single piece on the inner periphery of the container 6. The container may be a one- or two-piece container 6. According to FIG. 23, no perforated plate 32 is provided for carrying a filter disk 34, which may have a centrally upward bearing structure 34a for manual application. In the context of the invention, it is also possible for the top part 27 not to be a top container part in a literal sense, but merely a container adapter ring 114 so that the bottom part 26 forms the container 6.

It is advantageous to dispose a ring seal between the container 6 or bottom part 26 and the adapter ring 114 or top part 27 in order to guarantee a seal between them. According to FIG. 23, an O-ring 115 is provided as a seal, which is effective between the top edge of the bottom part 26 or container 6 and a radial shoulder surface 116 of the adapter ring 114 and whose sealing action is enforced by the vertically directed elastic tension with which the container 6 is slightly vertically compressed between the bottom and top rotating plates 14, 15.

When, after an evaporation or preparation process, the container 6 is removed laterally out of the holder 4, drops of condensation product present on the underside of the lid 24 are scraped off by the top edge of the container 6 and flow down the inner wall of the container 6 or adapter ring 114 into the collecting groove 111 without corrupting the material sample 47a or 47b.

A further or additional measure for preventing the formation of condensation product consists of disposing a material layer on the underside of the lid 24 or a plate on the lid 24 or associating with the container 6 an additional lid 24a made of microwave-absorbing material according to FIG. 13 so that the formation of condensation product is reduced or eliminated owing to increased heat.

It is also, according to FIG. 23, advantageous in terms of heat management alone to provide a plate made of microwave-absorbing material on the positioning surface for the container or containers 6.

The microwave-absorbing material is preferably a plastic, into which microwave-absorbing material has been introduced in a uniformly distributed manner. Said material may be, for example, carbon or graphite, as realized in the case of the plastic material, WEFLON, already known in this field. The proportion of heat-absorbing material is to be selected according to the desired temperature of the heat. It may be, for example, approximately 1 to 50%.

A further way in which the construction according to FIG. 23 differs from the constructions described above is that, for adapting containers 6 of differing heights to the holder 4, a base 117 is provided whose horizontal cross-sectional shape and size is substantially adapted to the horizontal cross-sectional shape and size of the container 6, so that it fits onto the associated positioning point 5. For reasons of cost, it is advantageous to form the base 117 from a bottom base part 117a made of a plastic with a lower heat resistance and a top base part 117b made of a plastic with a higher heat resistance and a heat-insulating property in order to guarantee the dimensional stability of the base even at the considerably high temperatures arising during operation. If a base plate 118 made of microwave-absorbing material is desired, it is advantageous to let said base plate in a form-fit manner into the top base part 117b. Such an insertion device is also, recommended between the base parts 117a and 117b to allow the base 117 to be handled as a structural unit. The base plate 118 and the top base part 117b are perforated.

In the constructions according to FIGS. 19 to 23, it is indicated in outline and by way of example how the inner and/or outer aeration of the holder 4 and the containers 6 need not be effected from the heating chamber 3 but may be effected directly from the environment of the device 1, namely through, in each case, one aeration line (see, for example, 40f in FIG. 21), which extends from outside, penetrating the heating chamber housing and the heating chamber 3, into the container 6. In all of the embodiments, it is possible to convey for cooling purposes into the heating chamber 3 and/or to the containers 6 not ambient air, but an inert gas so as to achieve explosion protection in the case of highly inflammable substances.

Figure 24:
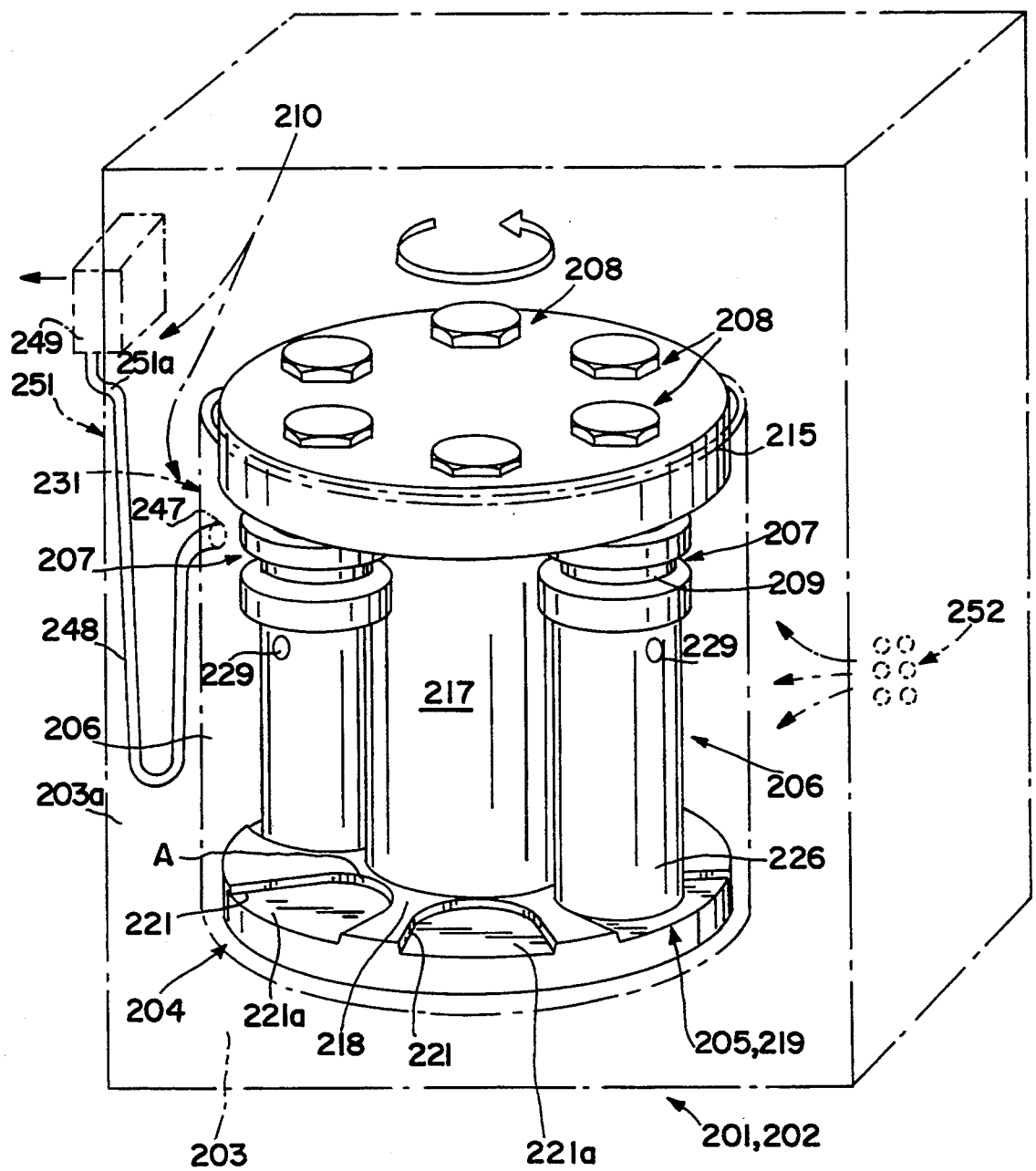
FIG. 24 a perspective front view of a device according to the invention having a holder for sample containers for decomposing and analysing sample material.
Figure 25:
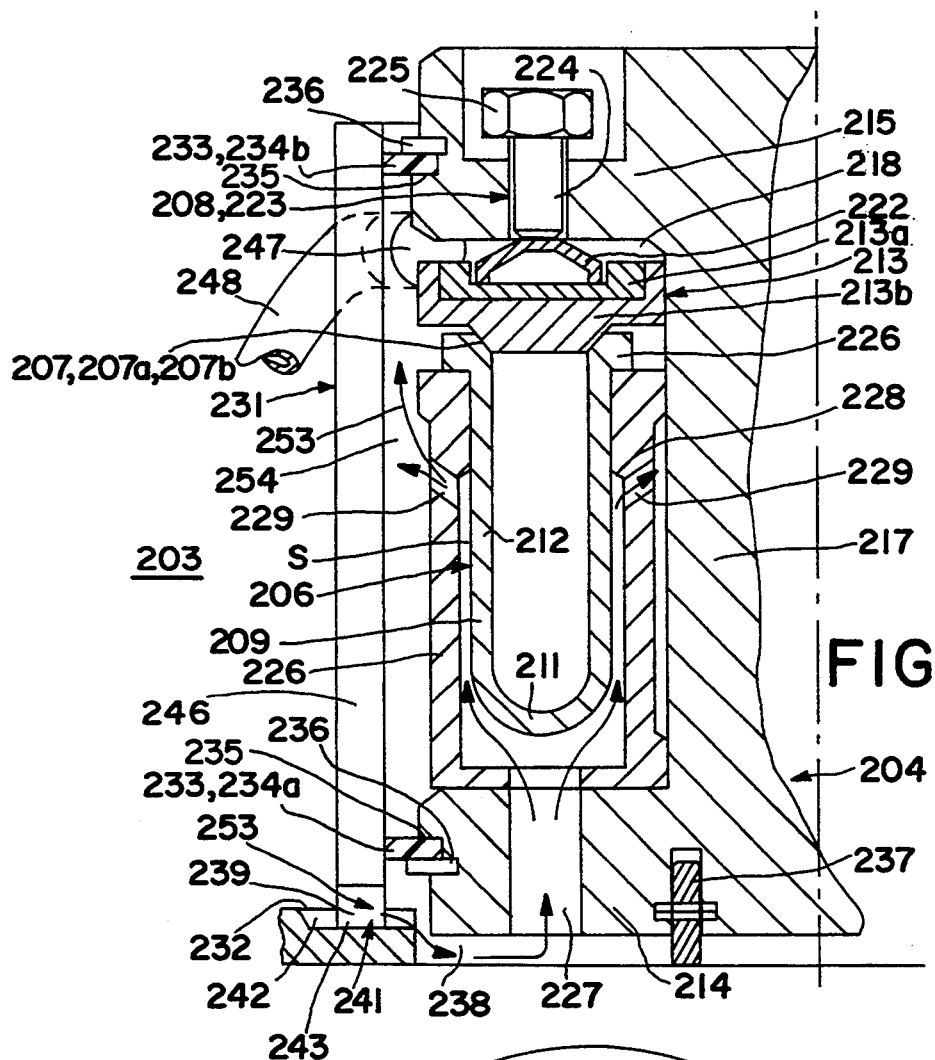
FIG. 25 a radial vertical partial section through the holder in the region of a positioning point for a sample container.
Figure 26:
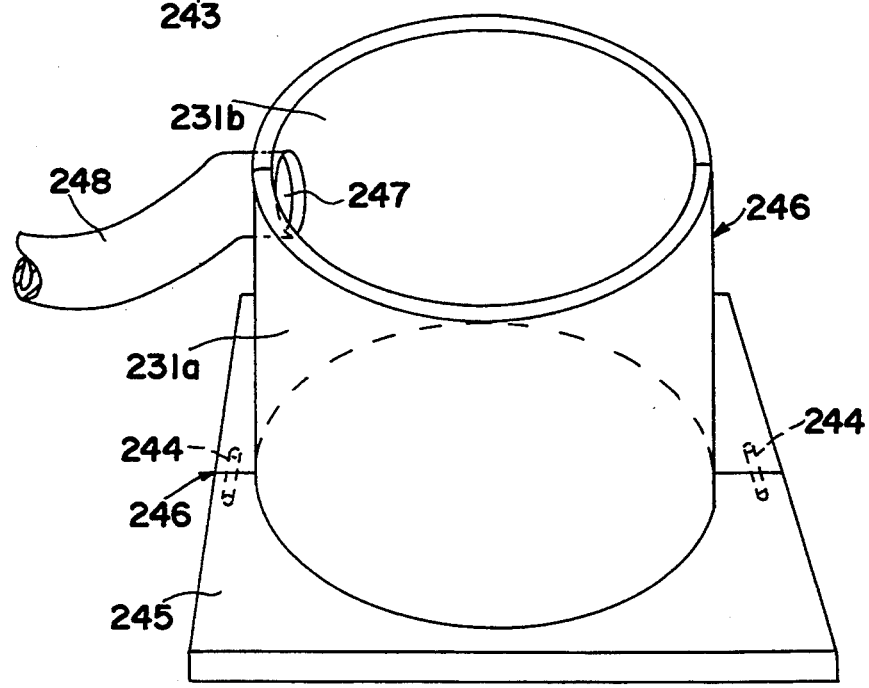
FIG. 26 a perspective view of a protective housing for the holder and the sample containers.

The principal parts of the device 201 according to FIGS. 24 to 26 are a microwave-operated heating appliance 202 with a heating chamber 203 which is closable by a door 203a, a holder 204 disposed in the healting chamber 203 and having a plurality of positioning points 205, preferably four or six, for sample containers 206, one pressure relief valve 207 per container 206, which automatically opens when a specific container internal pressure is exceeded and closes again on account of the tension of an elastic thrust piece, and one adjusting device 208 per valve 207 for adjusting its elastic initial tension, i.e. for setting the pressure at which the valve 207 automatically opens, and a cooling device 210 for the containers 206 and/or the holder 204 in the heating chamber 203 (FIG. 25).

The containers 206 are identical to one another in construction and each comprises a pot-shaped housing 209 with a housing base 211 and a cylindrical, vertically extending housing wall 212. The housing opening which is closable by a lid 213 is delimited by the top inner edge of the housing wall 212.

The valve 207 is disposed in the top region of the container 206, its valve member preferably being formed by the lid 213. When a specific internal pressure is exceeded in the container 206, the valve 207 opens automatically so that some of the internal pressure may escape outwards. This prevents the internal pressure exceeding a predetermined value and prevents the container 206 from becoming overloaded and exploding.

The seat of the valve 207 is constructed at the top inner edge of the cylindrical housing wall 212 and is formed by a downward converging, conical seating surface 207a which is disposed concentrically to the cylindrical housing wall 212. The cone angle is around 45° to 75°, preferably around 60°. The lid 213, which is insertable from above into the top inner edge of the cylindrical housing wall 212, has a correspondingly shaped conical sealing surface 207b.

The holder 204 is a rotating part having a bottom rotating plate 214 and a top rotating plate 215, between which the containers 206 are held. The rotating part may be driven in the sense of continuous rotation or a reciprocating swivelling movement, preferably through approximately 360°. The rotating plates 214, 215 are firmly connected to one another by a vertically extending connection part, here a connection tube 217, so that they project out radially beyond the connection tube 217 and form between them a common circular recess 218 or individual recesses for receiving the containers 206. There is preferably provided on the top of the bottom rotating plate 214, in the region of each positioning point 205, a guide 219 (FIG. 24) for the container 206 which positively effects a radially inward motional guidance with movement stop A upon lateral insertion of the container 6 between the rotating plates 214, 215. The guide 219 may be formed by an indentation 221 with a flat bottom surface 221a, whose width extending in a peripheral direction is adapted to the width of the preferably cylindrical container 206.

As is evident particularly from FIG. 25, the adjusting device 208 associated with each positioning point 205 is formed by an adjustable clamping device 223. In the construction according to FIGS. 24 and 25, the clamping device 223 is formed by a clamping screw 224 which is screwed into a threaded hole of the top rotating plate 215 so as to be accessible from above. The elastic thrust piece 222 is disposed on the lid 213 and between the latter and the clamping screw 224. The thrust piece 222 is preferably formed by a hollow cone-shaped moulding which may be disposed in a recess in the top of the lid 213. An application element 225 for a turning tool is disposed at the top end of the clamping screw 224. By suitably tightening the clamping screw 224, the valve 207 may be so adjusted that it opens and vents at a selected container internal pressure.

The pot-shaped housing 209 is held preferably in a suspended position in the holder 204. Said purpose is served in the present embodiment by a sleeve-shaped support 226, here taking the form of a cylindrical tube, in which the housing 209 is inserted from above and rests thereon by means of a housing flange disposed at its top end. With the exception of its top end region, the internal diameter of the support 226 is greater than the external diameter of the housing 209 so that there is between them a peripheral gap S. The height of the support 226 is greater than that of the housing 209 so that the housing base, in the suspended position, is at a distance from the bottom rotating plate 214. The bottom rotating plate 214 has coaxially at each positioning point 205 an, in particular, vertical through bore 227. Provided in the support 226 below its internal shoulder surface 228 is a plurality of through holes 29 which are distributed over the periphery and preferably extend obliquely upwards from inside to outside. The purpose of the through holes 227, 229 will be explained later. The support 226 may have a perforated base.

Associated with the holder 204 is a hollow cylindrical protective housing 231 which is large enough to surround the rotating plates 214,215 with a small radial clearance, the housing resting on the base 232 of the heating chamber 203 and its height being substantially adapted to the height of the holder 204.

Provided in each case between the bottom rotating plate 214 and the protective housing 231 and the top rotating plate 215 and the protective housing 231 is a seal 233 enabling a relative movement between the holder 204 and the protective housing 231 brought about by the rotation or swivelling of the holder 204. In the present construction, sealing rings 234a, 234b are provided, which are mounted from below or from above onto the associated rotating plate 214, 215, rest on a shoulder surface 235 and are locked against longitudinal displacement by a locking pin or split-pin 236.

In the present construction, the holder 204 is supported, so as to be capable of rotating or swivelling, on three wheels 237 which are uniformly distributed over the periphery and rotatably supported in the bottom rotating plate 214 and whose underside projects downwards so that there is a clearance 238 between the base 232 and the bottom rotating plate 214.

A radial through hole 239 is provided at the bottom end of the protective housing 231 below the bottom sealing ring 234a.

The protective housing 231 is locked against co-rotation by the holder 204 by means of a pin coupling 241 which effects positive locking. For said purpose, there may be provided in the base 232 a recess 242, into which a pin 243 projecting from the underside of the protective housing 231 engages in a positive-locking manner.

The protective housing 231 preferably comprises two half shells 231a, 231b (FIG. 26), which are lockable together in an aligned position by means of one or two further pin couplings 244 having at least one pin, disposed on the one half shell and at least one recess correspondingly disposed on the other half shell for receiving the pin. The protective housing 231 preferably has at its bottom end a possibly quadrangular flange 245 which, in the case of a two-piece construction, is similarly divided at the axial dividing seam 246. The pins of the pin coupling 243, 244 may be formed by screw-in screws.

Disposed in the protective housing 231 in the top region, but below the top sealing ring 234, is a radial connection hole 247 or a connection fitting which is connected by a tube 248 to a suction pump 249 (FIG. 24) disposed outside of the heating chamber 203. The tube 248 penetrates the heating chamber housing 251 in a sealed through hole 251a.

An air inlet 252, which may be formed by a plurality of small holes, is disposed in the heating chamber housing 251. It is possible to provide a plurality of through holes 239 and air inlets 252 distributed over the periphery.

To decompose sample materials introduced into the containers 206, the microwave generator (not shown) of the heating appliance 202 and the rotary operating mechanism for the holder 204 formed by a rotor are switched on. Uniform heating of all of the containers 206 and the sample material contained therein is effected. In the course of said treatment, excess pressures, which are mainly attributable to evaporation, and high temperatures arise in the containers. Since it is normally only the sample material which is to be heated by the microwaves, the material selected for the holder 204, the containers 206 and the protective housing 231 is a microwave-permeable material, preferably plastic, so that the parts in question are not heated by the microwaves. For the housing 209 and the lid 213, what is needed moreover is a highly corrosion-proof material which is resistant to acids produced by the sample material in the course of preparation, preferably polytetrafluoroethylene ( PTFE/Teflon) or tetrafluorocopolymer (TFM) or also quartz, ceramics or glass for the housing 209.

It is possible and possibly also advantageous to manufacture the housing 209 and/or the lid or a jacket surrounding the housing 209 from a material, in particular a plastic, which to a slight extent absorbs microwaves and so, during microwave radiation, generates a sensible heat which backs up the heating and also may prevent condensation product from forming in the container 206.

During heating, temperatures arise in the containers which are so high that the stability of a used plastic, e.g. PTFE, is reduced. Said problem could be countered by greater wall thicknesses but this would lead to an increase in overall sizes and manufacturing costs because the materials used are expensive.

The problem described above with regard to the stability of the used plastic affects not only the containers 206 but also the protective housing 231 and the holder 204 and in particular the top rotating plate 215 which, because of the prestressing of the elastic thrust piece 222, is subject to a stress which attempts to bend it upwards. The use of a highly temperature-resistant plastic for the holder 204 would lead to unacceptably high manufacturing costs.

Said problem is solved by the cooling device 210 according to the invention. Possibly at the same time as the microwave is switched on, the drive for the suction pump 249 is switched on so that said pump generates a cooling air stream 253 which enters the heating chamber 203 at the air inlet 252, extends transversely through the heating chamber 203 towards the radial through hole or holes 229, through the clearance 238, the through holes 227, the peripheral gap S, the radial through holes 229 and the annular free chamber 254 provided between the holder 204 and the protective housing 231 towards the tube 248 and the suction pump 249, from which chamber venting outwards is effected. The air flow path is the same as indicated by arrows in FIG. 2. The cooling stream 253 for the other containers 206 follows a corresponding course. By means of said air flow, the housings 209 are cooled in their bottom region over their entire surface, with the heat absorbed by the air stream being removed. It is advantageous for the housing base 211 to be hemispherical in shape. This results in a trouble-free advantageous distribution of the air stream towards the peripheral gap S.

It is possibly advantageous not to switch off the cooling device until some time after the microwave generator is switched off. In the above-described cooling device 210 according to the invention, there is therefore simultaneous cooling of the holder 204 with its individual parts, the protective housing 231 and the containers 206, with cooling in the case of the latter being effected externally.

The problem described above with regard to the stability of the plastic at operating temperature also applies to the lid 213. There is therefore associated with said lid a stabilizer, here in the form of a top lid disk 213a, (FIG. 25) which is disposed between the bottom lid disk 213b and the elastic thrust piece 222. The top lid disk 213a is made of a plastic of greater stability than the stability of the bottom lid disk 213b. The top lid disk 213a is preferably inserted in a recess of the bottom lid disk 213b.

I claim:

1. A device for evaporation treatment of sample material in a container, said device having a microwave-operated heating appliance, a heating chamber and a holder for at least one container in the heating chamber, the container being connected to a line, characterized in that the line has in the peripheral region of the container a releasable line connection which is established by insertion movement on insertion of the container into the holder and is severed by removal movement on removal of the container from the holder as a result of relative displacement of portions of the line connection.

2. A device according to claim 1, characterized in that the line connection is oriented such that insertion and removal movement of the container is directed substantially horizontally as well as transversely to an operating side and the axis of the line connection extends substantially horizontally.

3. A device according to claim 1, characterized in that the line connection is a plug-in connection.

4. A device according to claim 1, characterized in that the container comprises a pot-shaped bottom part and a lid.

5. A device according to claim 4, characterized in that the line penetrates a lid on the container and opens out into a cavity in the bottom portion of the container.

6. A device according to claim 1, characterized in that the line penetrates the holder in a lead-in hole.

7. A device according to claim 5, characterized in that the lid is on the holder and the line connection is provided between the lid and the bottom portion of the container.

8. A device according to claim 1, characterized in that the holder has two vertically spaced-apart, substantially horizontal seating surfaces between which the container is insertable and selectively removable substantially horizontally.

9. A device according to claim 8, characterized in that one of the seating surfaces is vertically movable and is acted upon by a spring force in a downward direction.

10. A device according to claim 1, characterized in that a guide is associated with the holder for guiding the container into a positioning point in the holder and a stop is provided for delimiting the insertion movement in the positioning point.

11. A device according to claim 1, characterized in that associated with the device are a measuring device for measuring a condition in a region which includes the container and the line and an electronic control device with an evaluation device, the control device being constructed and arranged to switch off the device during operation when the measured condition reaches a a predetermined value.

12. A device according to claim 1, characterized in that a conduit for a flowable substance is disposed and extends helically from top to bottom in the container.

13. A device according to claim 1, characterized in that the container is hung in a suspended arrangement on the holder by means of a suspension device.

14. A device according to claim 13, characterized in that the suspension device has holding limbs which engage laterally under suspension shoulders of the container, and in that an insertion opening is provided for insertion of the container between the holding limbs.

15. A device according to claim 13 or 14, characterized in that associated with the suspension device is a vertically elastically yielding closure part for the container, said closure part being clampable against an opening edge of the container.

16. A device according to claim 1, characterized in that a collecting groove for condensation product is provided on an inner wall near the top of the container.

17. A device according to claim 1, characterized in that associated with the heating chamber is a cooling device comprising a gas feed device for generating a cooling gas stream which extends in the heating chamber from an inlet opening to an outlet opening.

* * * * *